(12) United States Patent
Teshigawara et al.

(10) Patent No.: US 6,609,019 B1
(45) Date of Patent: Aug. 19, 2003

(54) PHYSIOLOGICAL MAGNETIC FIELD MEASURING INSTRUMENT FOR MEASURING MAGNETIC FIELD AT PLURAL POSITIONS OF LIVING BODY

(75) Inventors: Kenji Teshigawara, Hitachinaka (JP); Hiroyuki Suzuki, Hitachinaka (JP); Keiji Tsukada, Kashiwa (JP); Kazuhisa Machida, Kawasaki (JP); Akihiko Kandori, Kokubunji (JP); Tsuyoshi Miyashita, Kokubunji (JP); Hitoshi Sasabuchi, Mito (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/493,798

(22) Filed: Jan. 28, 2000

(30) Foreign Application Priority Data

| Feb. 2, 1999 | (JP) | ............................................ 11-024918 |
| Feb. 8, 1999 | (JP) | ............................................ 11-030159 |
| Mar. 19, 1999 | (JP) | ............................................ 11-075000 |

(51) Int. Cl.$^7$ ................................................. A61B 5/05
(52) U.S. Cl. ........................ 600/409; 324/244; 324/248; 324/307
(58) Field of Search ........................... 600/409; 324/307, 324/244, 248; 128/924, 925

(56) References Cited

U.S. PATENT DOCUMENTS 5,092,343 A * 3/1992 Spitzer et al. .............. 128/925
6,336,043 B1 * 1/2002 Suzuki et al. ................ 324/200

FOREIGN PATENT DOCUMENTS

| JP | 4-319334 | 11/1992 |
| JP | 5-146416 | 6/1993 |
| JP | 10-5186 | 1/1998 |

* cited by examiner

*Primary Examiner*—Marvin M. Lateef
*Assistant Examiner*—Runa Shah Qaderi
(74) *Attorney, Agent, or Firm*—Mattingly, Stanger & Malur, P.C.

(57) ABSTRACT

The present invention, in the physiological magnetic field measuring instrument, recognizes characteristic waveforms (for example, heart beats) repeatedly appearing by physiological activity from measured signal waveforms, registers one of measured heart beats as a reference waveform, evaluates the difference degree of each measured heart beat data from the reference waveform, and executes the averaging process using only waveforms whose difference degrees are less than the allowable value. The present invention registers waveforms whose difference degrees are more than the allowable value as abnormal data and puts them into the display enabled state. Discrimination information is as signed to measurement conditions necessary for measuring the physiological magnetic field and data analysis conditions and when the discrimination information is designated for measurement, the measurement conditions and analysis conditions can be read. By doing this, the physiological magnetic field measuring instrument independently selects good or defective data automatically, and a reliable automatic averaging process can be obtained, and the data processing and operation can be simplified.

4 Claims, 32 Drawing Sheets

PHYSIOLOGICAL MAGNETIC FIELD MEASURING INSTRUMENT FOR MEASURING MAGNETIC FIELD AT PLURAL POSITIONS OF LIVING BODY

BACKGROUND OF THE INVENTION

The present invention relates to a physiological magnetic field measuring instrument for measuring the magnetic field of a living body generated due to the internal current relating to the cerebral nerve activity and myocardial activity of a living body.

Conventionally, a multi-channel (many magnetic sensors arranged in a matrix) physiological magnetic field measuring instrument using a superconducting quantum interference device, which is a magnetic sensor for measuring a minute magnetic distribution generated from a living body inferring the active current position in the living body, and imaging the distribution is well known.

A conventional example such as a magnetometer or gradiometer is disclosed, for example, in Japanese Patent Application Laid-Open 4-319334, Japanese Patent Application Laid-Open 5-146416, and Japanese Patent Application Laid-Open 10-5186.

This kind of physiological magnetic field measuring instrument is being put into practical use and as a condition necessary for practical use, it is desired to detect a minute magnetic field generated from a living body by removing the effect of noise as much as possible. For that purpose, to remove the effect of environmental magnetic noise, a magnetic field measuring instrument is installed inside a magnetic shield room or for example, the following measuring signal process is known.

For example, the physiological magnetic field measuring instrument described in Japanese Patent Application Laid-Open 10-5186 indicates an example of measurement of the magnetic field generated from the brain, and proposes a fluxmeter (composed of a plurality of magnetic sensors) for measuring a minute magnetic field generated from a patient, and an electrocardiograph for measuring an electrocardiac waveform of the patient. A match of the magnetic data measured by the fluxmeter with the cardiac data measured by the electrocardiograph is obtained, and when the match of the two is high, the magnetic data is handled as defective data, but when the match is low, it is retained as one which is not affected by noise. These operations are performed repeatedly, and after termination of the predetermined count, the retained physiological magnetic field measured data is added and averaged in data collection units.

The aforementioned prior art is one relating to the operation principle concerning a physiological magnetic imaging device and the description does not include technical problems and solving means for practical realization. The aforementioned prior art relates to the physiological active current generated inside the brain but does not include concrete description concerning other parts.

Furthermore, the aforementioned prior art is attempted, when performing an averaging process for cerebral magnetic data using the physiological magnetic field measuring instrument (cerebral magnetic meter), to remove the noise synchronized with the heart beat simultaneously using the electrocardiograph, but it neither considers a case that the physiological magnetic field measuring instrument is used for a magnetocardiograph meter nor intends to independently use the physiological magnetic field measuring instrument.

An object of the present invention is to provide a physiological magnetic measuring method and a physiological magnetic field measuring instrument so that the magnitude of magnetic field at a plurality of measuring positions can be measured easily and satisfactorily.

Another object of the present invention is to provide a physiological magnetic field measuring instrument realizing highly reliable automatic average processing by automatically selecting good or defective data by magnetocardiograph measurement or cerebral magnetic measurement independently, using the physiological magnetic field measuring instrument without simultaneously using the electrocardiograph.

Still another object of the present invention is to provide a method, when there is sudden abnormal data in measured data as a result of physiological magnetic field measurement, for automatically selecting and displaying it and using the abnormal data as information useful for diagnosis.

Furthermore, the present invention contributes to integrated automation from reading of measured data (signal waveform) of the physiological magnetic field measuring instrument to data analysis, and simply executes operation and condition setting.

SUMMARY OF THE INVENTION

According to the present invention, a method for measuring the magnetic field generated from the inside of the living body of a patient at a plurality of positions has a means for displaying a plurality of measuring positions on the display screen, a means for selecting the position to be displayed from the displayed measuring positions, and a means for displaying information concerning the magnitude of magnetic field at the selected position, and displays the plurality of measuring positions together with the existence of selection in the display state that the information concerning the magnitude of magnetic field is displayed. The present invention provides the channel item corresponding to the channel displayed on the analytical data display unit in the operation area display unit. The present invention also provides the other measuring items.

According to the present invention, the physiological magnetic field measuring instrument for measuring the magnetic field generated from the inside of the living body of a patient has a waveform recognition means for recognizing characteristic waveforms repeatedly appearing by physiological activity from the measured signal waveforms, a reference waveform registration means for registering one of the characteristic waveforms repeatedly appearing as a reference waveform, a waveform evaluation means for evaluating the difference degree of each of the characteristic waveforms repeatedly appearing from the reference waveform, and a calculation means for executing the averaging process using only the waveforms whose difference degrees are less than the allowable value.

By use of such a constitution, from actually measured signal waveforms of each person, the reference waveform is set. Such a method provides the following advantages. Namely, since there is an individual difference in the state of the characteristic waveform (for example, heartbeat waveform) repeated by physiological activity, when the reference waveform is identified from signal waveforms repeated by true physiological activity of each person like the system of the present invention, a reference waveform actually suited to each person can be set better than when the reference waveform is temporarily set from the standard simulated waveform.

As a method for identifying the reference waveform of the present invention, for example, a method for registering the n-th waveform (for example, the first waveform) from the waveform recognized by the waveform recognition means as a reference waveform may be considered. When the identified reference waveform is accidentally sudden defective data, waveform data having a difference degree less than the allowable value cannot be read by the predetermined count. If this occurs, when the reference waveform identifying operation is performed until waveform data suited to the reference waveform can be identified by reexecuting registration of the reference waveform and evaluation of the difference degree in the same way as with the previous one after remeasurement or newly selecting the aforementioned reference waveform and reexecuting the averaging process, the above problem can be solved.

DETAILED DESCRIPTION OF THE PREFERRED EMBODIMENTS

Figure 1:
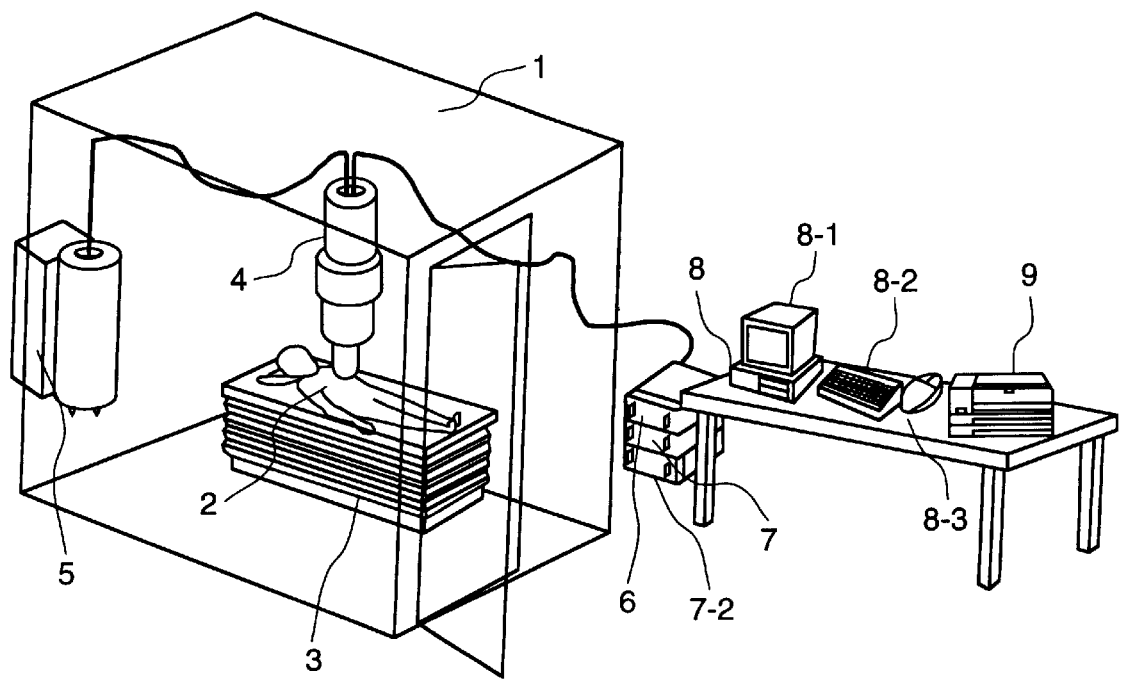
FIG. 1 is a schematic block diagram showing an embodiment of a physiological magnetic field measuring instrument which is an applicable object of the present invention.

FIG. 1 is a schematic block diagram showing an embodiment of a physiological magnetic field measuring instrument which is an applicable object of the present invention.

As a physiological magnetic field measuring instrument of the present invention, as an example, a magnetocardiograph measuring instrument (magnetocardiograph meter) for measuring the magnetic field distribution of a heart is used and to remove the effect of environmental magnetic noise, the physiological magnetic field measuring instrument is installed in a magnetically shielded room 1. A patient 2 who is a living body is generally subjected to magnetocardiograph measurement in the state that he lies on his back on a bed 3, though he may be measured in the state that he lies on his face.

The living body surface (in the case of the chest, generally a face parallel with the chest wall) of a patient is regarded as almost parallel with the surface of the bed 3 and the surface is regarded as parallel with the x-y plane of the orthogonal coordinate system (x, y, z). Actually, the chest of the patient is a curved surface and inclined at the same time. However, for simplicity of explanation, it is regarded as almost parallel.

Above the chest of the patient 2, a dewar 4 (or cryostat) filled with liquid helium (a refrigerant) is arranged, and the dewar 4 houses a plurality of magnetic sensors including a SQUID (superconducting quantum interference device) and a detection coil connected to the SQUID. Liquid helium is continuously supplied from an automatic replenishment device 5 installed outside the magnetically shielded room 1. Automatic Refilling Apparatus The magnetic sensor outputs a voltage having a specific relation with the magnitude of a physiological magnetic field (which can be considered as magnetic flux density) which is generated from the patient 2 and detected by the detection coil, and the output is input to an FLL (flux locked loop)

circuit 6. The FLL circuit 6 cancels (by a magnetic lock) a change in the physiological magnetic field (physiological magnetism) input to the SQUID via the feedback coil so as to keep the SQUID output constant. By changing the current flowing through the feedback coil to a voltage, a voltage output having a specific relation with a change in the physiological magnetic field signal can be obtained. Since a method for detecting via the feedback coil is used, a weak magnetic field can be detected with high sensitivity.

The aforementioned output voltage is input to an amplifier, filter, and amplifier (AFA) 7, and the output thereof is sampled and converted from analog to digital by an A-D converter 7-2, and fetched by a calculator 8.

The calculator 8 is composed of a personal computer, and numeral 8-1 indicates a display unit thereof, 8-2 a keyboard, and 8-3 a mouse.

The mouse 8-3 is used to move a cursor on the screen and select a processing object. This operation also can be performed by operating the keyboard. The calculator is connected to a printer 9 and the contents displayed on the display unit 8-1 can be output to an output paper. The printer may output either color or monochromatic print. In this embodiment, a color printer is connected.

The calculator 8 can perform various processes and processing results are displayed on the display unit 8-1.

The calculator 8 shown in FIG. 1 is an embodiment, but the calculator is not so limited. For example, it may be provided with a display having a touch panel or may use another coordinate instruction device instead of the mouse (for example, a pointing device such as a trackball or joystick). When applicable, a calculator connected via a general telegraph circuit may be used.

Figure 2:
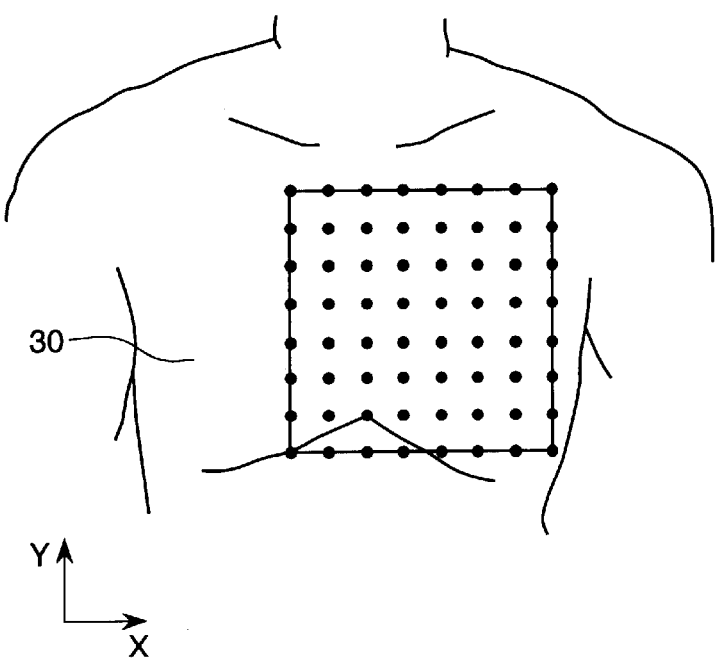
FIG. 2 shows the location relationship between a magnetic sensor and the chest which is a part to be measured of a patient.

FIG. 2 shows the location relationship between magnetic sensors and a chest 30 of the patient, 2 to be measured. The displayed points indicate the positions of magnetic sensors arranged in a matrix in the dewar, that is, measuring positions. Each of the measuring positions may be called a channel.

As shown in FIG. 2, in this embodiment, the direction of the body axis connecting the head part of the patient 2 and the foot part is the y direction and the lateral direction of the patient 2 is the x direction. Each magnetic sensor is recognized by a serial number from 1 to 64 and the position on the lattice. With respect to the serial numbers 1 to 64, the magnetic sensor in the upper left corner is assigned 1 (1st channel), the magnetic sensors on the right are sequentially assigned 2, 3, 4, - - - , and the magnetic sensor in the upper right corner is assigned 8 (8th channel). Then, the magnetic sensors in the second row are assigned 9, 10, - - - starting from the left end and the magnetic sensor at the end of the second row is assigned 16 (16th channel). The numbers are assigned in the same way hereafter and the magnetic sensor in the lower right corner is assigned 64 (64th channel). When each magnetic sensor is to be recognized by the position on the lattice, it is represented by n-th row, m-th column. The magnetic sensor 1 is represented by 1st row, 1st column and the magnetic sensor 64 is represented by 8th row, 8th column.

Figure 3:
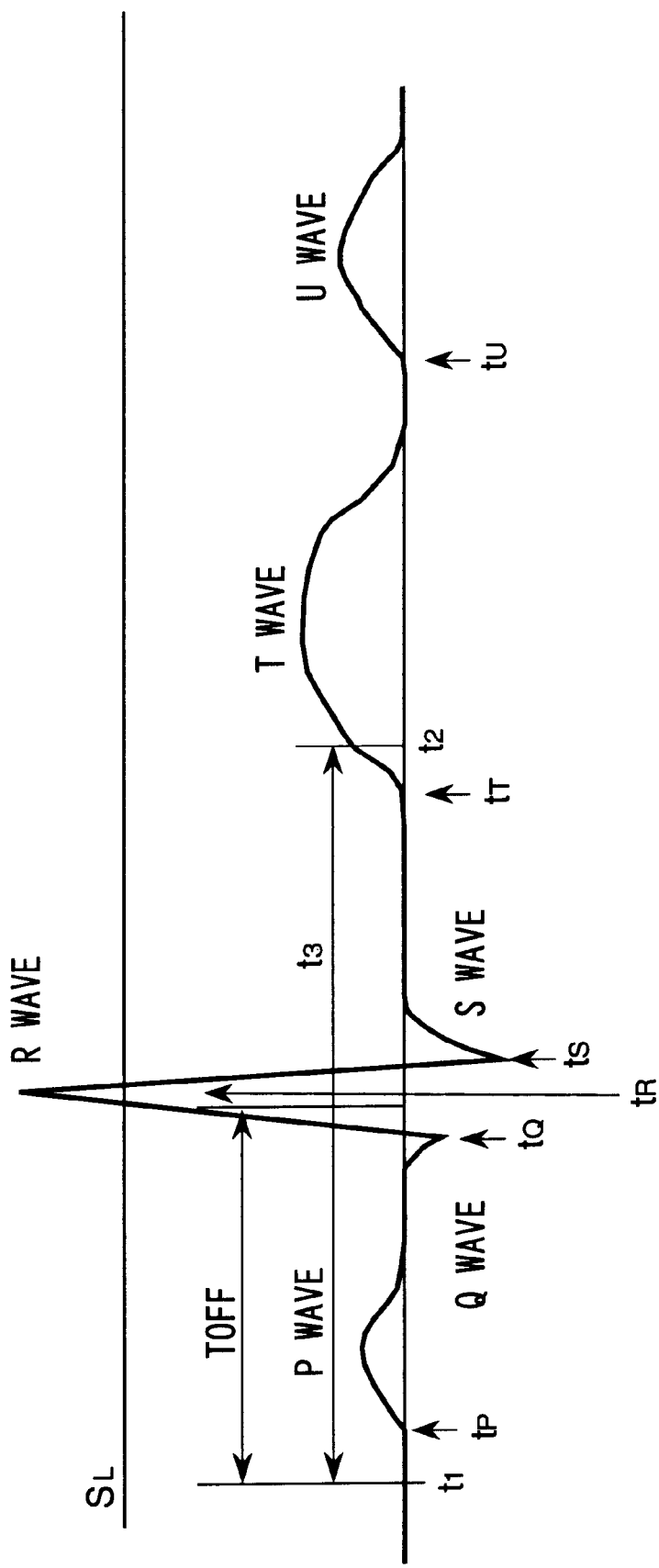
FIG. 3 shows an example of the waveform pattern of a magnetocardiograph signal of one heart beat detected by a magnetic sensor.

FIG. 3 shows an example of the waveform pattern of a magnetocardiograph signal of one heartbeat detected by a magnetic sensor. The basic waveform pattern of a magnetocardiograph signal corresponds to the waveform pattern of an electrocardiogram and the P wave, QRS wave, and T wave can be ascertained. The P wave indicates the process of excitement of the atrium muscle by the stimulative wave emitted from the sinus tuber, the QRS wave indicates the excitement process of both the left and right ventricular muscles, and the T wave indicates the recovery process of the ventricular muscles from excitement. The electric physiological meaning of the U wave is not fully understood and many points are left unascertained due to a small amplitude.

According to the present invention, in the waveform separated as a signal of one heartbeat, the start times of the P wave, T wave, and U wave may be defined as tP, tT, and TU respectively from the top time of the signal. The time of the QRS wave is defined as tQ, tR, and tS respectively.

The predetermined time (tOFF) is traced back from the point of time when the leading edge of the QRS wave matches the threshold value SL and the data until the point of time t2 when only the predetermined time T3 elapses from the traced-back point of time t1 is added by the predetermined count. This is averaging, and the predetermined time T3 is called averaging time and tOFF is called offset time. The magnetocardiograph wave data may be integrated within the predetermined time range.

As physical amounts obtained by the calculation process for a signal at each measuring position (sensor position) of the magnetic field from a living body, there are the magnetic flux density at a certain time, the time integrated value of the magnetic flux density in the time interval by time, and in the case of magnetocardiograph measurement, the propagation delay time which is a time from the standard time to the peak position time of the QRS wave.

A map created by connecting points where the magnetocardiograph waveform value, that is, magnetic flux density is equal is called an isomagnetic diagram. Since each channel is roughly set, when the gap of equal magnetic lines, that is, the difference in magnitude of magnetic field is preset and equal magnetic lines are drawn by linear interpolation between the channels, a map which is more suited to diagnosis can be created.

The magnetocardiograph waveform data may be integrated within the predetermined time range. A map created by connecting points (channels) where the time integral values are equal is called a time integral diagram.

In the time characteristics of signal data detected by each sensor, the time from the point of time t1 to the peak position period of time (tR) of the QRS wave is called the propagation delay time, and a map created by connecting points where the propagation delay times are equal is called a propagation delay time diagram. The period of time t1 may be decided by detecting the peak position period of time of the QRS wave and setting the period of time as a standard.

The isomagnetic diagram, time integral diagram, and propagation delay time diagram are reconfigured in correspondence with the plane where the sensors are arranged. However, it is possible to reconfigure as three-dimensional mapping by taking the characteristic amount of each calculation process in the perpendicular direction to the plane.

Next, a concrete example of the summary of the present invention will be explained.

Measurement of a physiological magnetic signal and data display and analysis are all executed by the calculator 8 and operated by the display unit 8-1, the keyboard unit 8-2, and the mouse 8-3.

Figure 4:
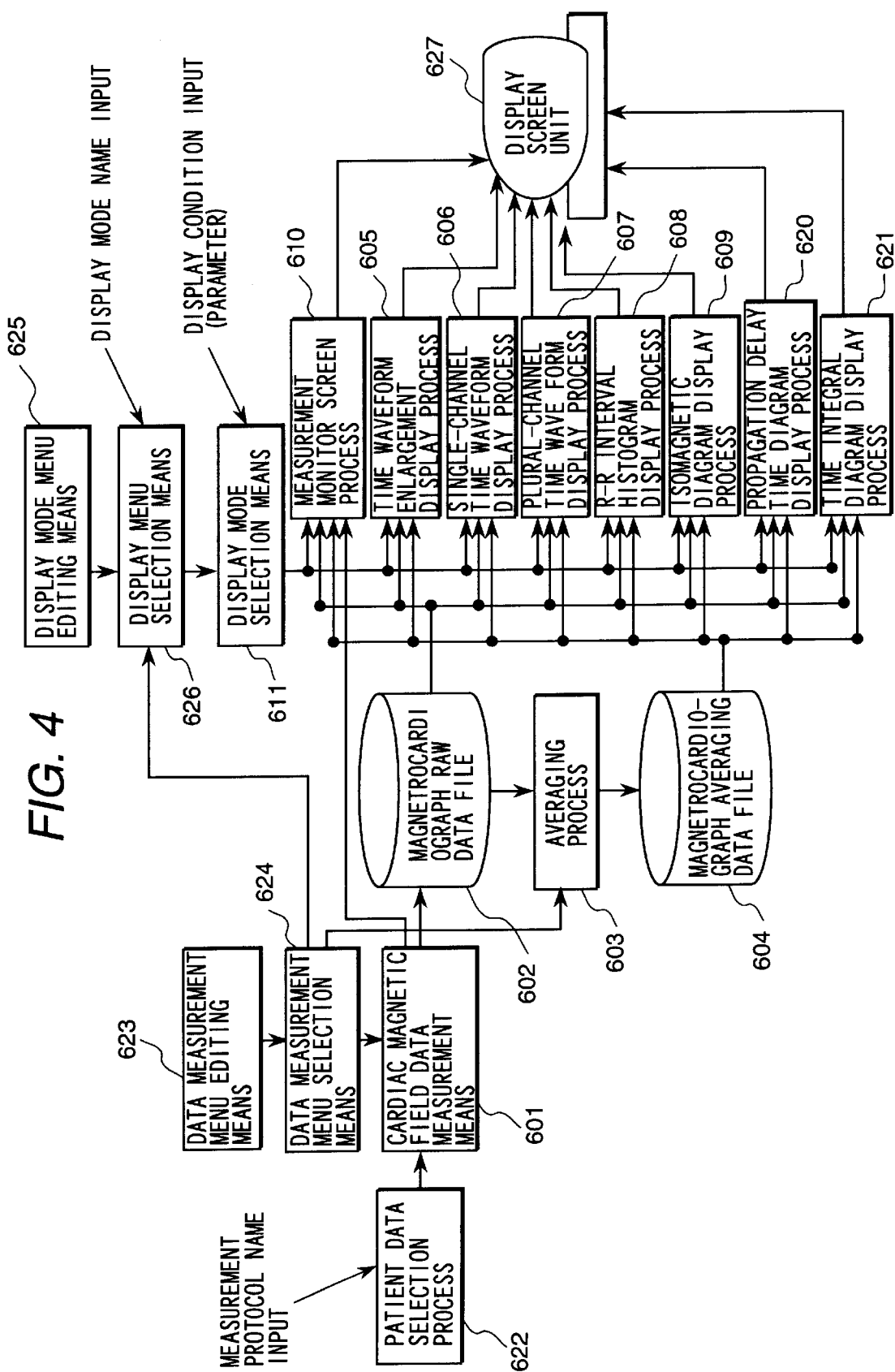
FIG. 4 is a block diagram of an apparatus for realizing the present invention.

FIG. 4 is a block diagram of an apparatus for realizing the present invention. This example indicates a magnetocardiograph meter as an example, though it is not limited to it and a cerebral magnetic meter for measuring the cerebral magnetic field may be applied.

As shown in FIG. 4, a patient is selected first by a patient data selection process 622, and the magnetocardiograph data of the selected patient is measured by a magnetocardiograph data measuring means (SQUID, magnetic sensor) 601 and fetched by a magnetocardiograph raw data file 602. The magnetocardiograph data measuring means 601 can display the magnetocardiograph data of the patient on the image display unit in real time as a time waveform and by doing this, it can be ascertained whether the SQUID correctly detects. To provide an easy operation, to the input gain and output gain which are measurement parameters, high-pass filter, low-pass filter, band elimination filter, and a set of sampling interval and sampling time, names indicating the data measuring object can be assigned and it is executed by a data measurement menu editing means 623. A set of measurement parameter values named by the data measurement menu editing means 623 is designated by a name from an operator by a data measurement menu selection means 624 and it can be transferred to the magnetocardiograph data measuring means 601 by interpreting it as a set of measurement parameter values corresponding to it. The magnetocardiograph raw data file 602 measured by the magnetocardiograph data measuring means 601 is subjected to the predetermined data display process by selecting the corresponding screen display processor (the measuring monitor screen processor 610, the time waveform enlargement display processor 605, the single channel time waveform display processor 606, the plural-channel time waveform display processor 607, the R-R histogram display processor 608, the isomagnetic diagram display processor 609, the propagation delay time diagram display processor 620, or the time integral diagram display processor 621) by a display mode selection means 611 and then displayed on a display screen unit 627. In this case, the display mode selection means 611 receives various display parameters depending on the processing contents of the image display processor.

However, when a disease which is a target is decided, the display parameter can be fixed. Therefore, the set of display parameter values is named and registered beforehand by a display mode editing means 625, and the name of the set of display parameter values registered by a display menu selection means 626 is received when executing the screen display processor, and it can be transferred to the display mode selection means 611 by interpreting as a corresponding display parameter.

By driving the averaging means, the averaging process is performed for the measured data (time waveform). The averaging process is a process of executing calculation of adding and averaging for each heartbeat (time waveform) among the collected magnetocardiograph signals (measured data) and forming a smooth waveform reduced in noise. The averaging process can be automated by recognizing the waveform pattern of the magnetocardiograph raw data file 602.

In the data measurement menu editing means 624, the conditions for the averaging process for automatically recognizing the waveform pattern and executing averaging are registered and immediately after the magnetocardiograph raw data file 602 is generated by the magnetocardiograph data measuring means 601, the averaging process is automatically performed and a magnetocardiograph averaging data file 604 can be generated. The measured data generated and averaged like this is stored in the data file 604 and can be displayed via the aforementioned various screen display processors 610, 605, 606, 607, 608, 609, 620, and 621 in place of the magnetocardiograph raw data file 602.

In FIG. 4, the patient data selection processor 622, the data measurement menu editing means 623, the data menu selection means 624, the display mode menu editing means 625, the display menu selection means 626, the the screen display processors 610, 605 to 609, 620, and 621, the magnetocardiograph raw data file 602, the averaging processor 603, the magnetocardiograph averaging data file 604, and the display mode selection means 611 comprise the calculator 8. The screen display processing states executed by the aforementioned screen display processors will be explained hereunder by referring to FIGS. 5 to 30.

Figure 5:
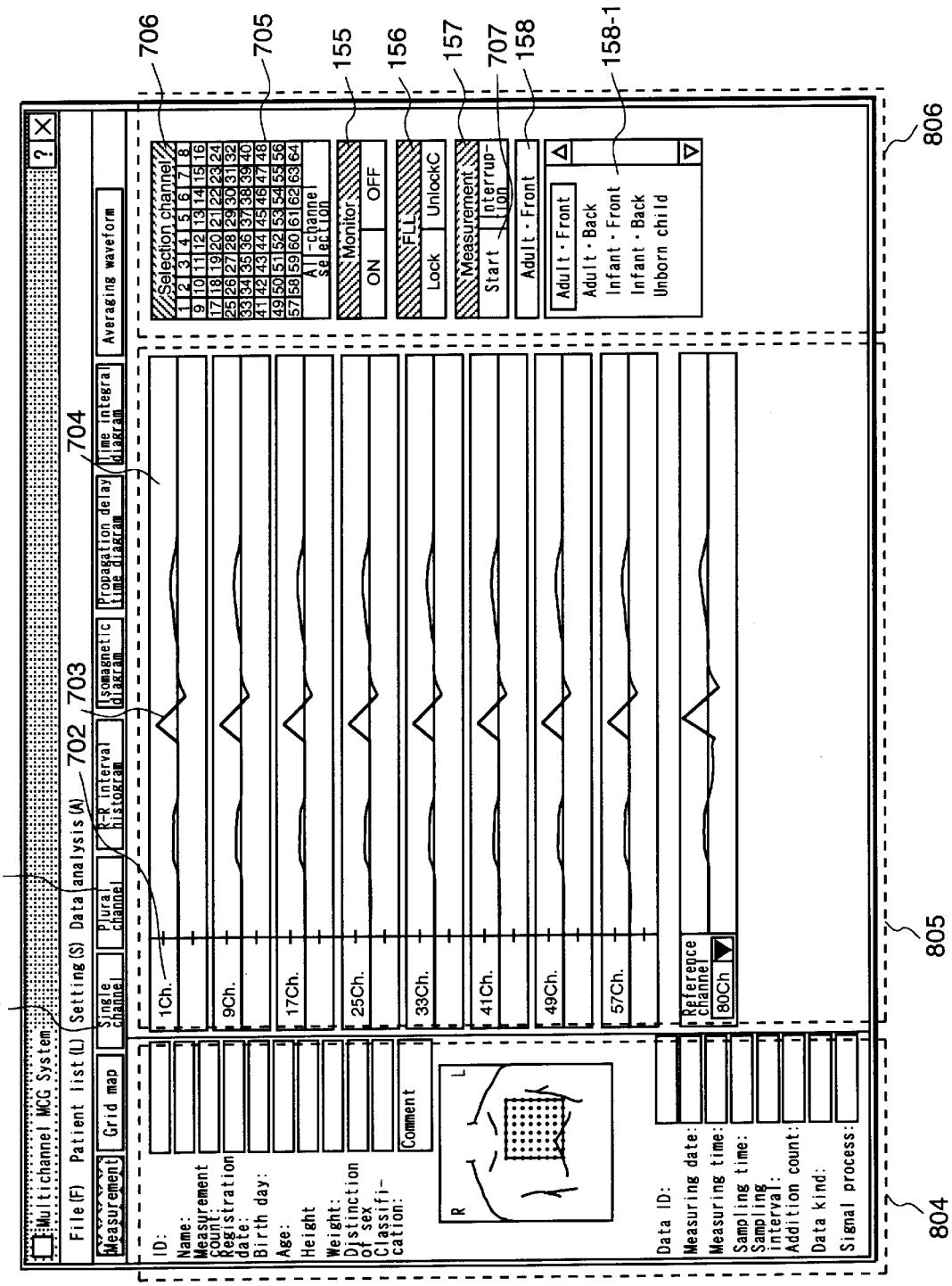
FIG. 5 shows a screen example of data display process contents executed by a measuring monitor screen processor.

FIG. 5 shows a screen of data display process contents executed by the measuring monitor screen processor 610 (hereinafter, called a measurement screen) which is displayed when the magnetocardiograph field is measured. The basic layout of the operation screen will be described by using the screen as an example. In an information display area (display unit) 804 on the left of the measurement screen, information of a patient who is an object of magnetic field measurement is shown.

The center of the screen is a measuring monitor display area 805 and the measured magnetocardiograph waveform is monitored and displayed.

On the right of the screen, an operation display area 806 capable of setting various conditions concerning magnetocardiograph measurement by cursor operation such as the mouse and keyboard is formed, and on the upper part of the area, a selection channel area (a channel display means) 706 is formed. When the desired channel, for example, the channel number 1, 9, 17, 25, 33, 41, 49, or 57 is designated by operating the mouse via a channel button (channel designation means) 705, the time waveform of magnetic signals collected by the magnetic sensor equivalent to the channel number is monitored and displayed.

With respect to monitoring of the waveform, when the ON button of a monitor button 155 is pressed, for example, between 0.5 s and 2 s, fetching of a signal and updating of the waveform are repeated at designated times, and the magnetocardiograph signal of a patient is monitored.

On the monitor, the time waveform is generally displayed in correspondence with the SQUID sensor position (channel) on a grid map. Thus, when a strong magnetic field is externally applied to the SQUID, the magnetic field is trapped in the loop of the SQUID device, or the magnetic field lock by the FLL circuit is released, and errors of those sensors can be easily discriminated by an operator using the grid map.

The grid map is useful in checking the magnitude of external magnetic field noise and checking that the location relationship between a patient and the dewar (that is, sensor) is appropriate. When a magnetic signal from the heart of a patient is monitored, the amplitude of the time waveform of the sensor positioned on the diagonal line passing the upper left and lower right becomes smaller, the time waveform of the sensors positioned under it is reversed in polarity, and the peak of the R wave whose amplitude is largest looks down. This suggests that there is a current dipole in the direction along the diagonal line and by ascertaining the position of the sensor whose signal is weak, the location relationship between the patient and the dewar can be known.

When the OFF button of the monitor button 155 is pressed, the updating of the waveform is stopped.

With respect to an FLL button 156, when the Lock button or Unlock button is clicked, for the 64 SQUID sensors, the magnetic field can be locked or unlocked. In this case, when one of the buttons is pressed, the state is kept unchanged until the other button is pressed. By doing this, the unselected malfunction state can be avoided.

The data measurement parameters are the sampling time (measuring time) and interval, input gain of the AFA circuit, output gain, low-pass filter, high-pass filter, and band elimination filter set value. These parameters can be decided by the data measurement object and purpose by the data measurement menu editing diagram which will be described later, so that they are named (discrimination information) and registered in the data measurement menu. Therefore, by selecting a registered name (discrimination information) by clicking by the mouse, a parameter for measurement can be automatically set in the magnetocardiograph measurement system. For example, in the example shown in FIG. 5, a data measurement menu of "adult, front", "adult, back", "infant, front", "infant, back", and "unborn child" is registered and "adult, front" is selected.

Figure 6:
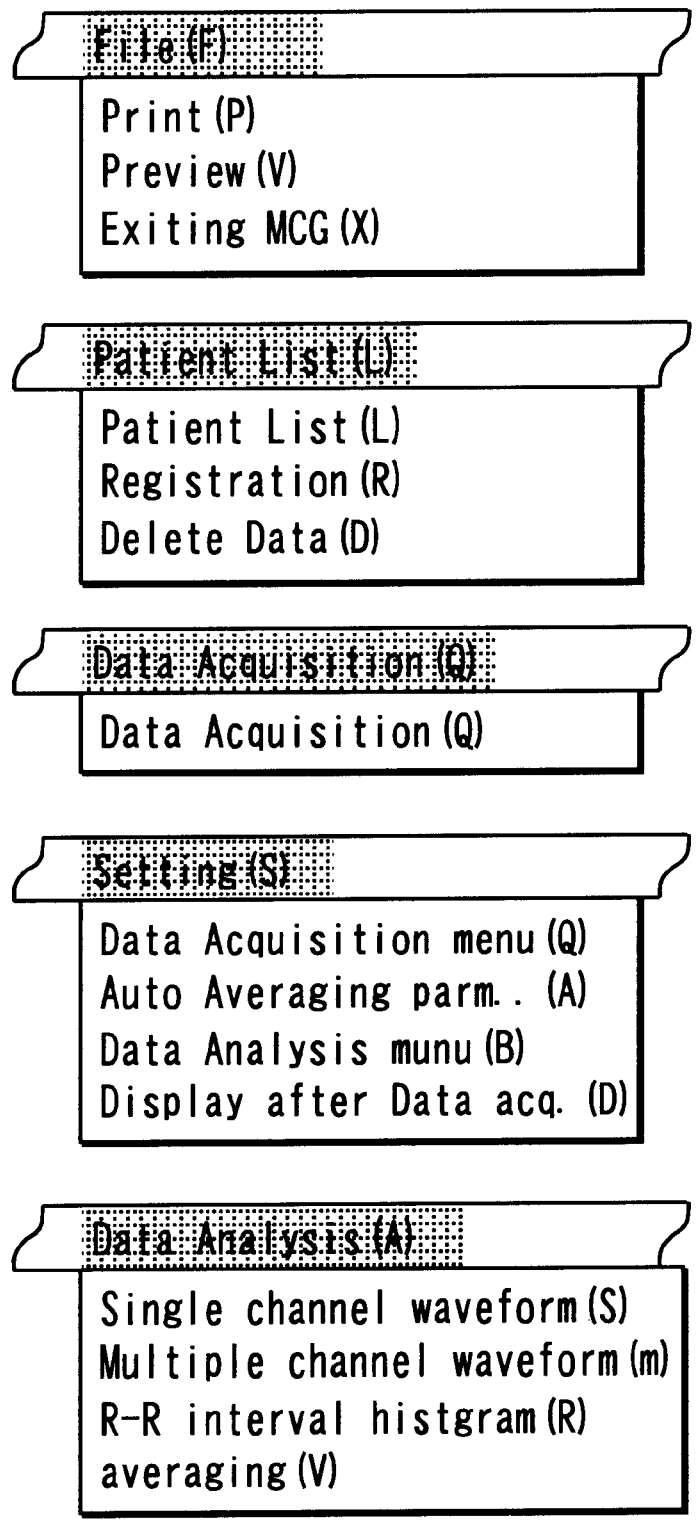
FIG. 6 shows a menu item for each menu in the menu bar provided on the upper part of the screen.

FIG. 6 shows the menu item for each menu in the menu bar provided on the upper part of the screen. In the menu bar, there are menus of "file (F)", "patient list (L)", "data measurement (Q)", "setting (S)", and "data analysis (A)" and when the mouse cursor is dragged onto these menus and the left button of the mouse is clicked, the menu item list shown in FIG. 6 can be opened. To select the desired menu item from the menu item list, it is desirable to drag the mouse cursor onto the target menu item and click it.

When the menu item "print (P)" is selected in the "file (F)" menu, the contents displayed on the screen are printed by the printer as they are, and when the menu item "preview (V)" is selected, the contents printed by the menu item "print (P)" are displayed on the screen and the print contents can be ascertained. When the menu item "magnetocardiograph system termination (X)" is selected, the magnetocardiograph system program terminates.

When the menu item "patient list (L)" is selected in the "patient list (L)" menu, the patient list screen which is not shown in the drawing is displayed. When the menu item "patient registration (R)" is selected, the patient registration dialog which is not shown in the drawing is displayed and the patient is registered. When the menu item "patient deletion (P)" is selected, the patient information selected by the cursor in the patient list displayed at present and the data belonging to the patient are all deleted. When the menu item "data deletion (D)" is selected, among the data belonging to the patient selected by the cursor in the patient list displayed at present, the data selected by the cursor in the data list displayed in the lower half of the patient list screen is deleted.

Figure 7:
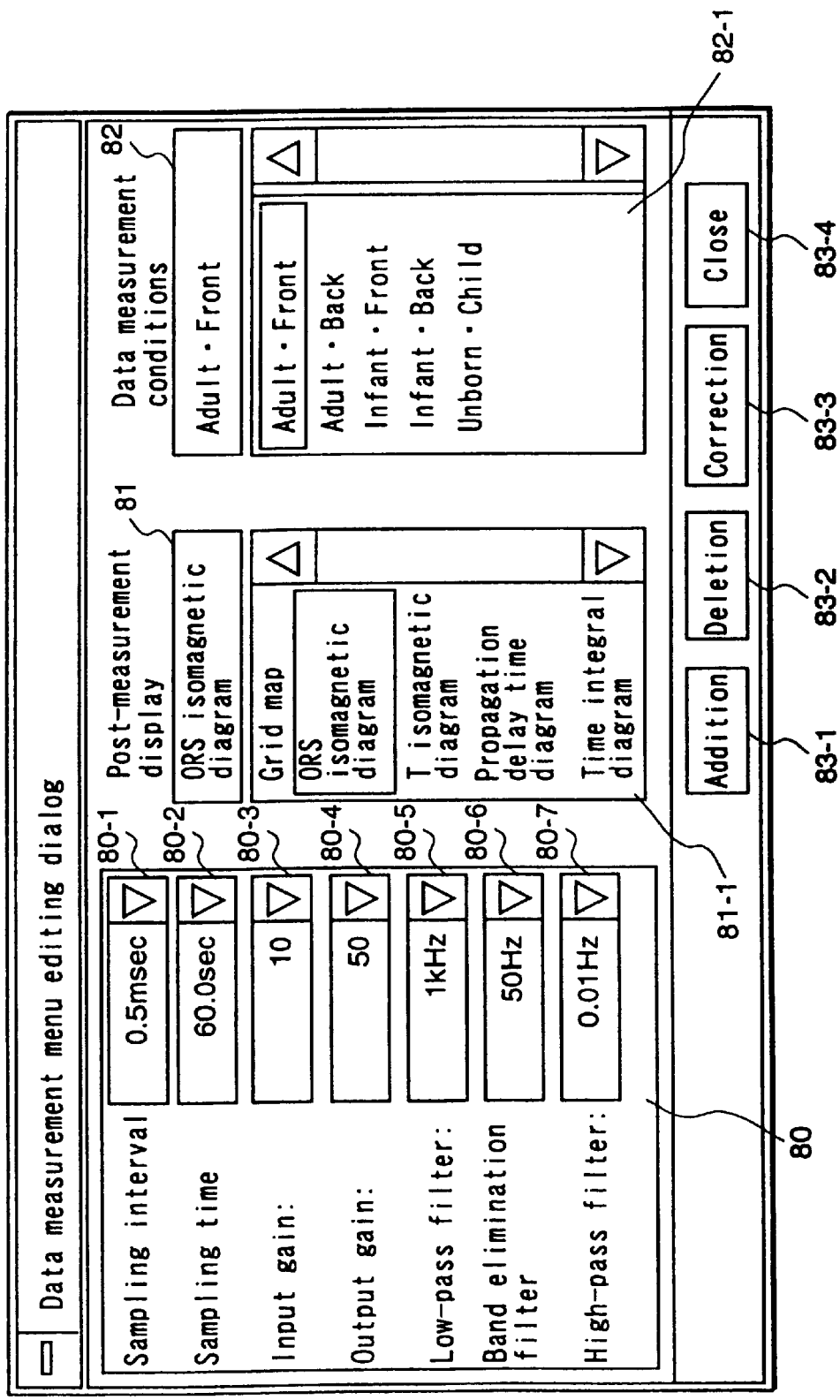
FIG. 7 shows a display screen example of a data measurement menu editing dialog.
Figure 14:
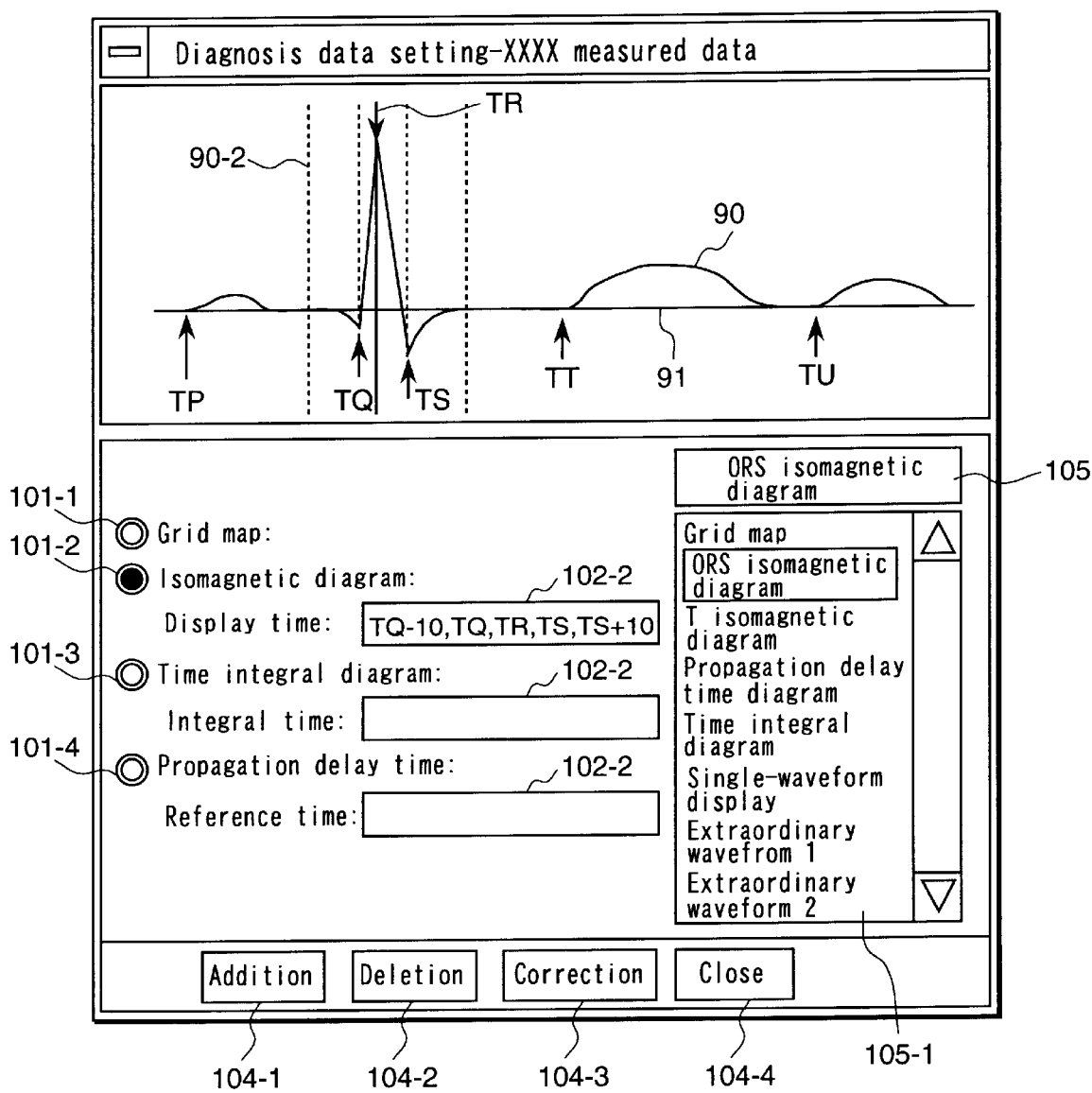
FIG. 14 shows a display screen example of a diagnostic data setting dialog.
Figure 21:
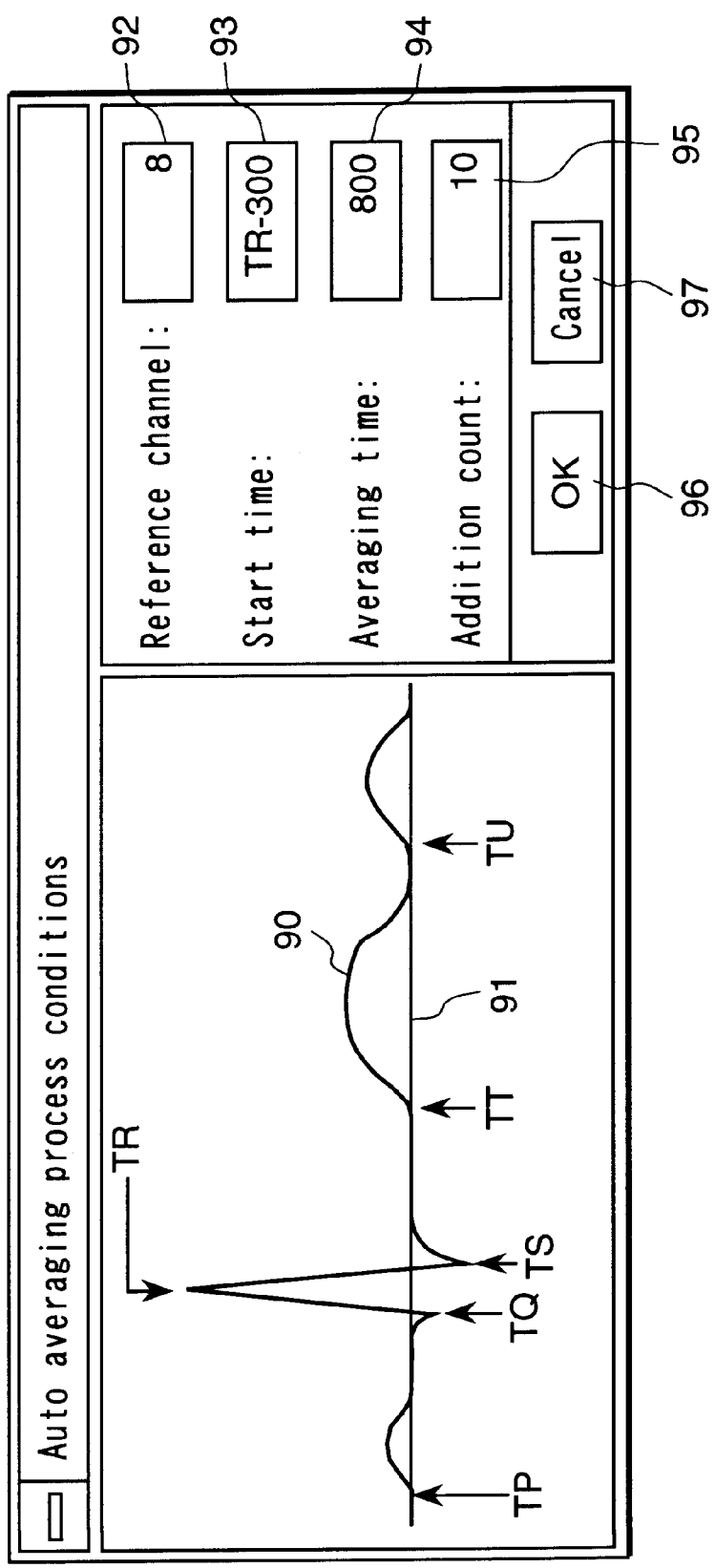
FIG. 21 is a drawing showing a dialog for setting automatic averaging process conditions.

When the menu item "data measurement (Q)" is selected in the "data measurement (Q)" menu, the data measurement screen shown in FIG. 5 is displayed and signal monitoring starts. When the menu item "data measurement menu (Q)" is selected in the "setting (S)" menu, the data measurement menu editing dialog shown in FIG. 7 is opened. When the menu item "automatic averaging condition (A)" is selected, the automatic averaging condition analog shown in FIG. 21 is opened. When the menu item "data analysis menu (B)" is selected, the diagnosis data setting screen shown in FIG. 14 is opened. When the menu item "post-measurement display condition (D)" is selected, the data measurement menu editing dialog shown in FIG. 7 is opened and only the post-measurement display items can be input. These setting screens and dialogs will be described later in detail.

Figure 8:
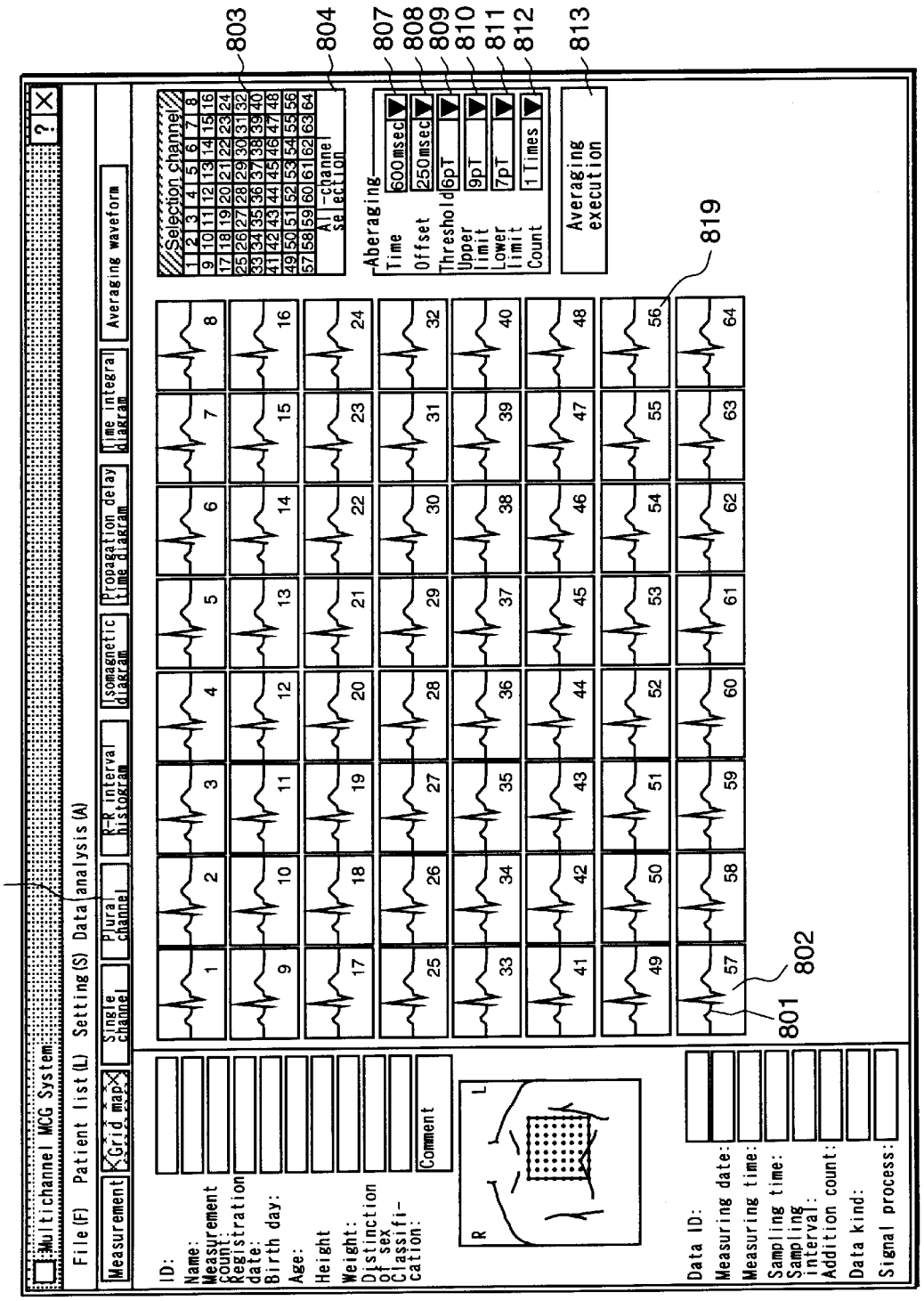
FIG. 8 shows an all-channel time waveform display screen example.
Figure 9:
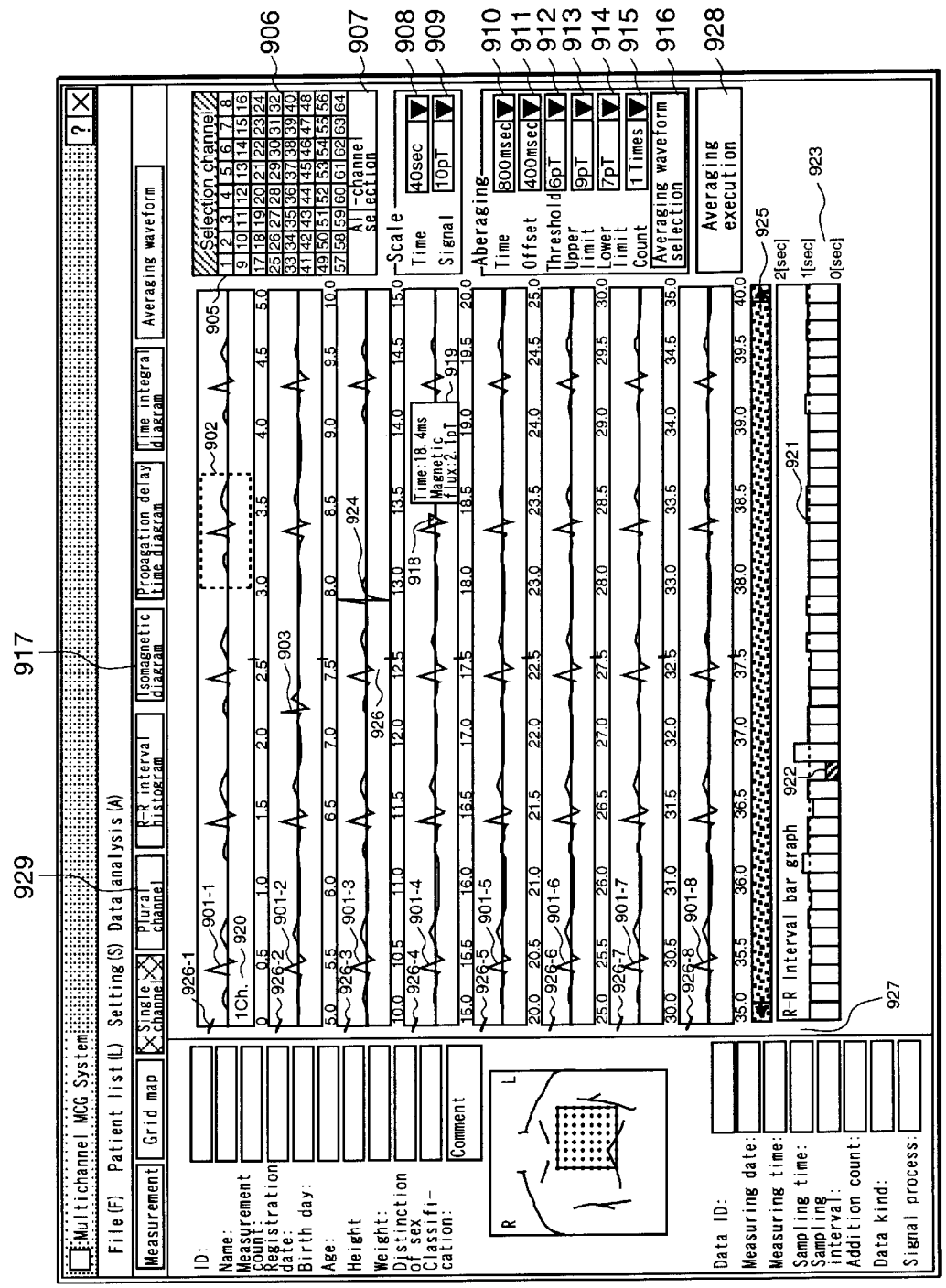
FIG. 9 shows a single channel time waveform display screen example.
Figure 10:
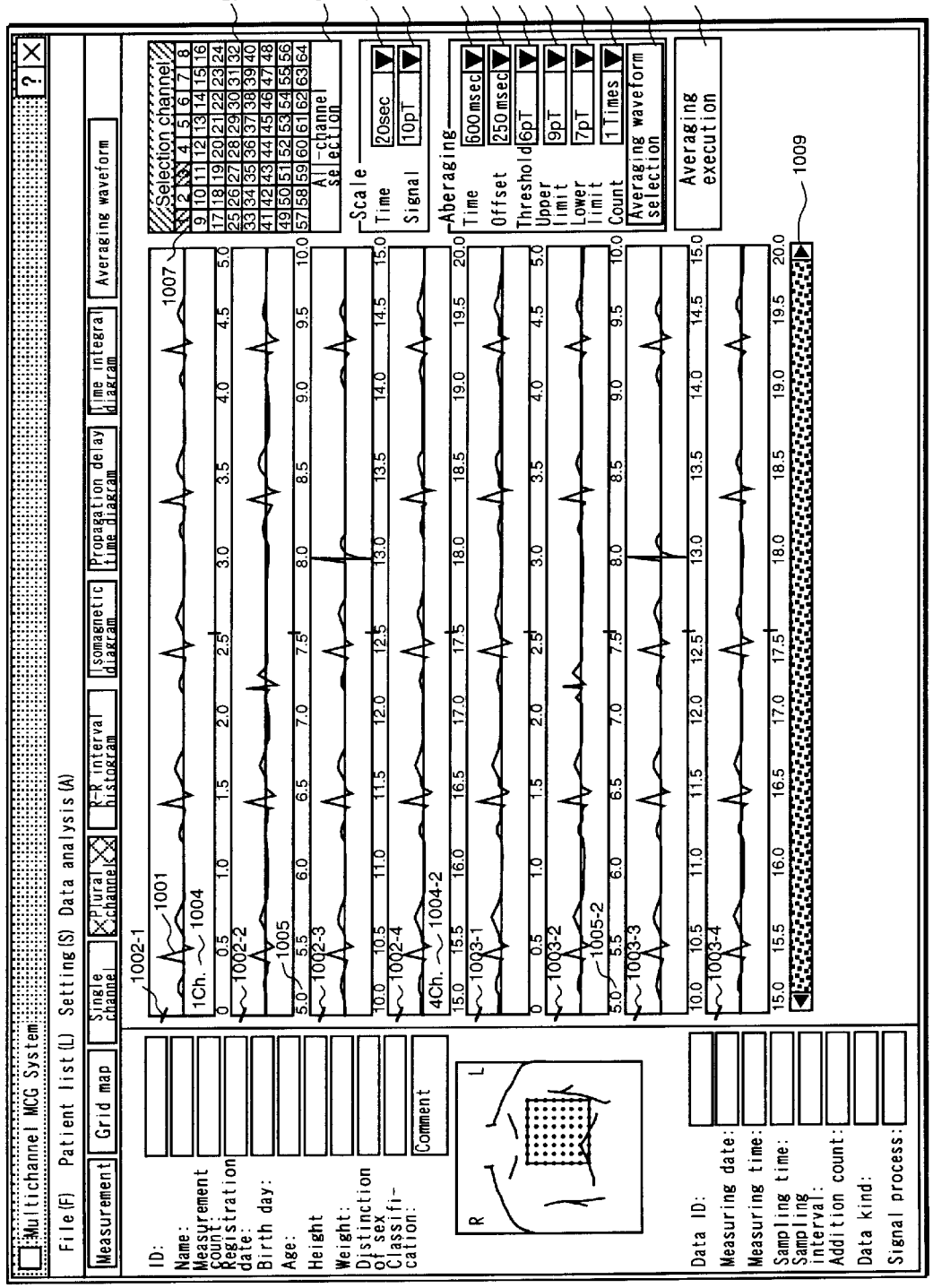
FIG. 10 shows a plural-channel time waveform display screen example.
Figure 11:
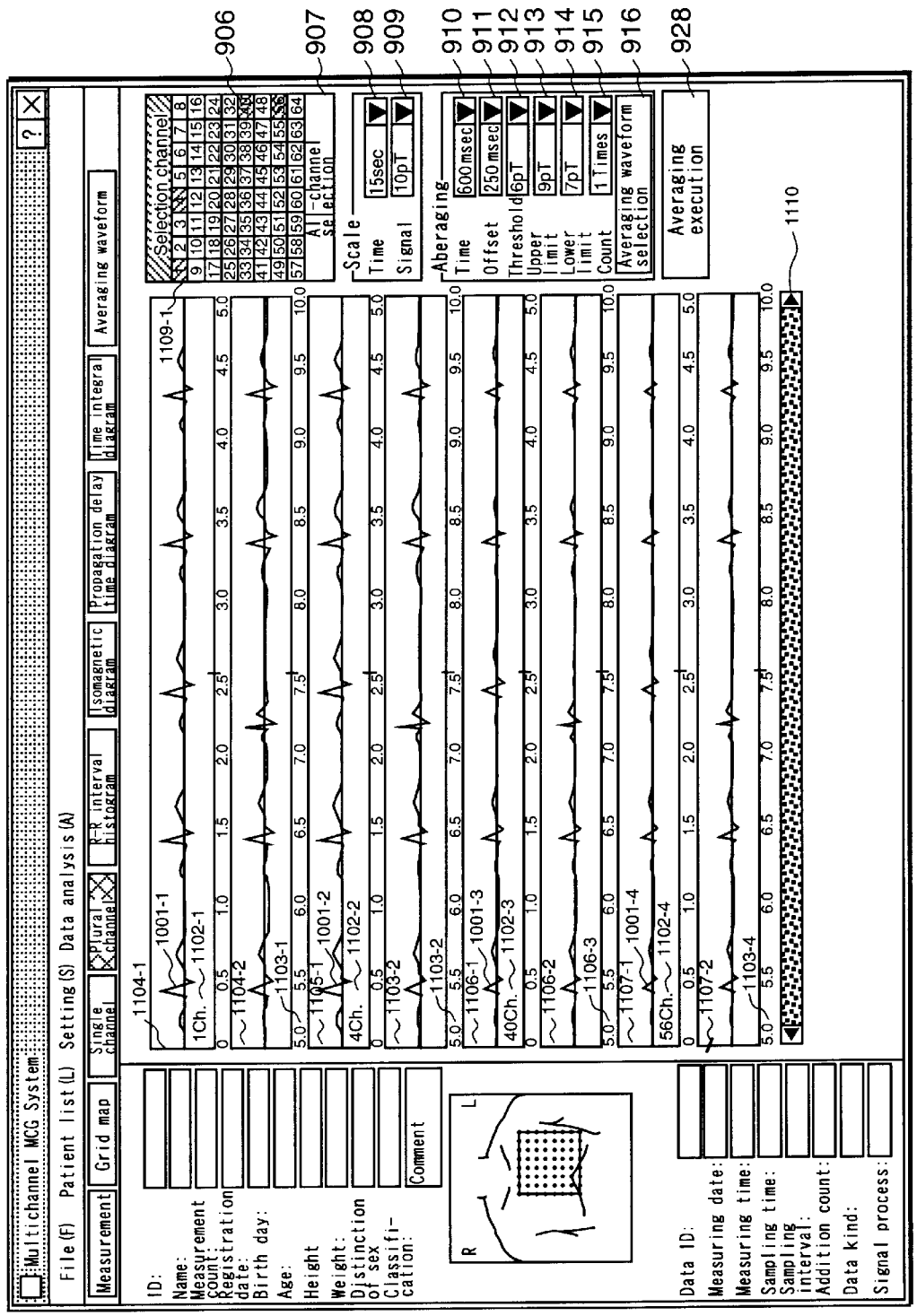
FIG. 11 shows an example that 4-channel time waveforms are displayed on a plural-channel time waveform display screen.
Figure 13:
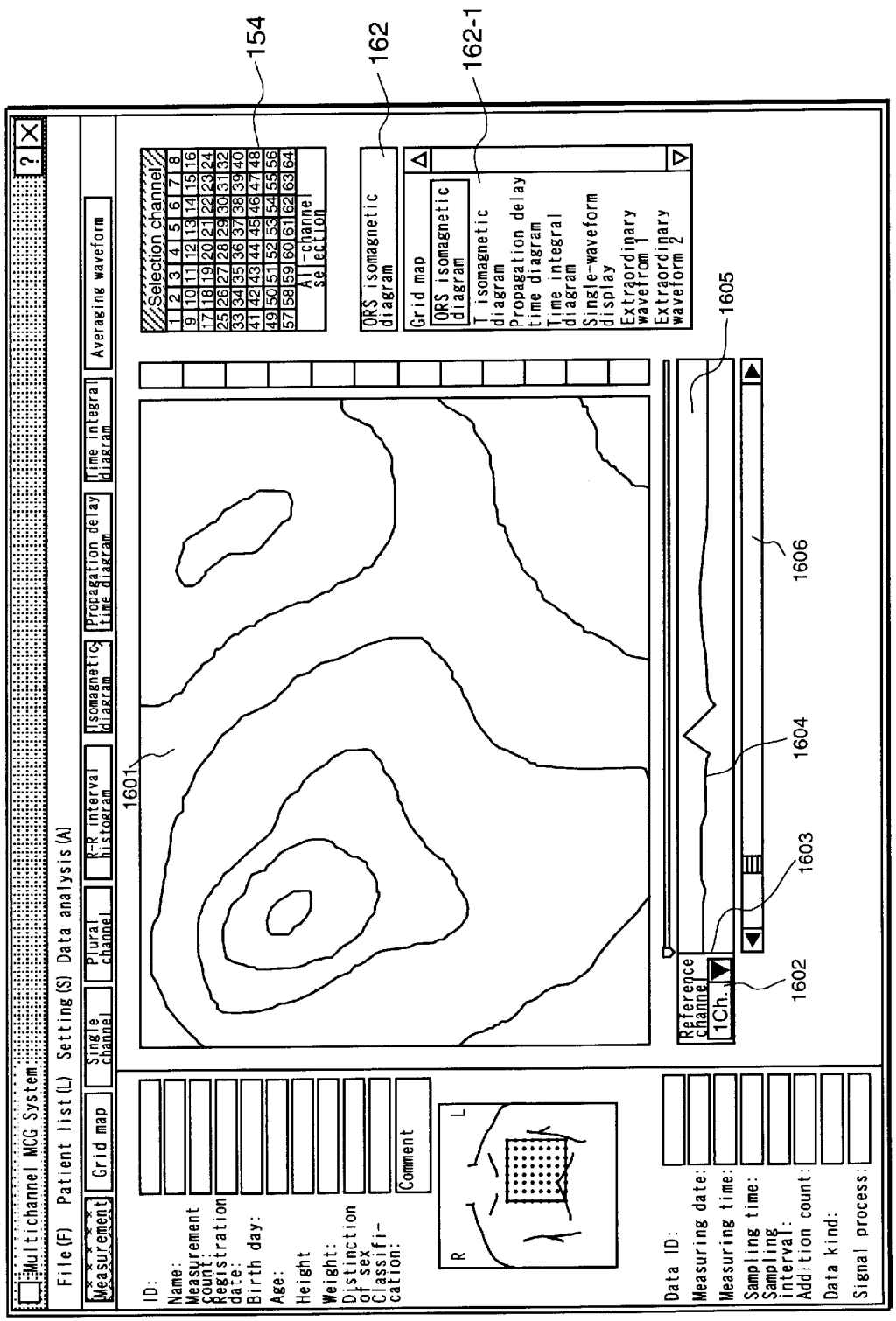
FIG. 13 shows a display screen example of an equivalent magnetic field chart.
Figure 15:
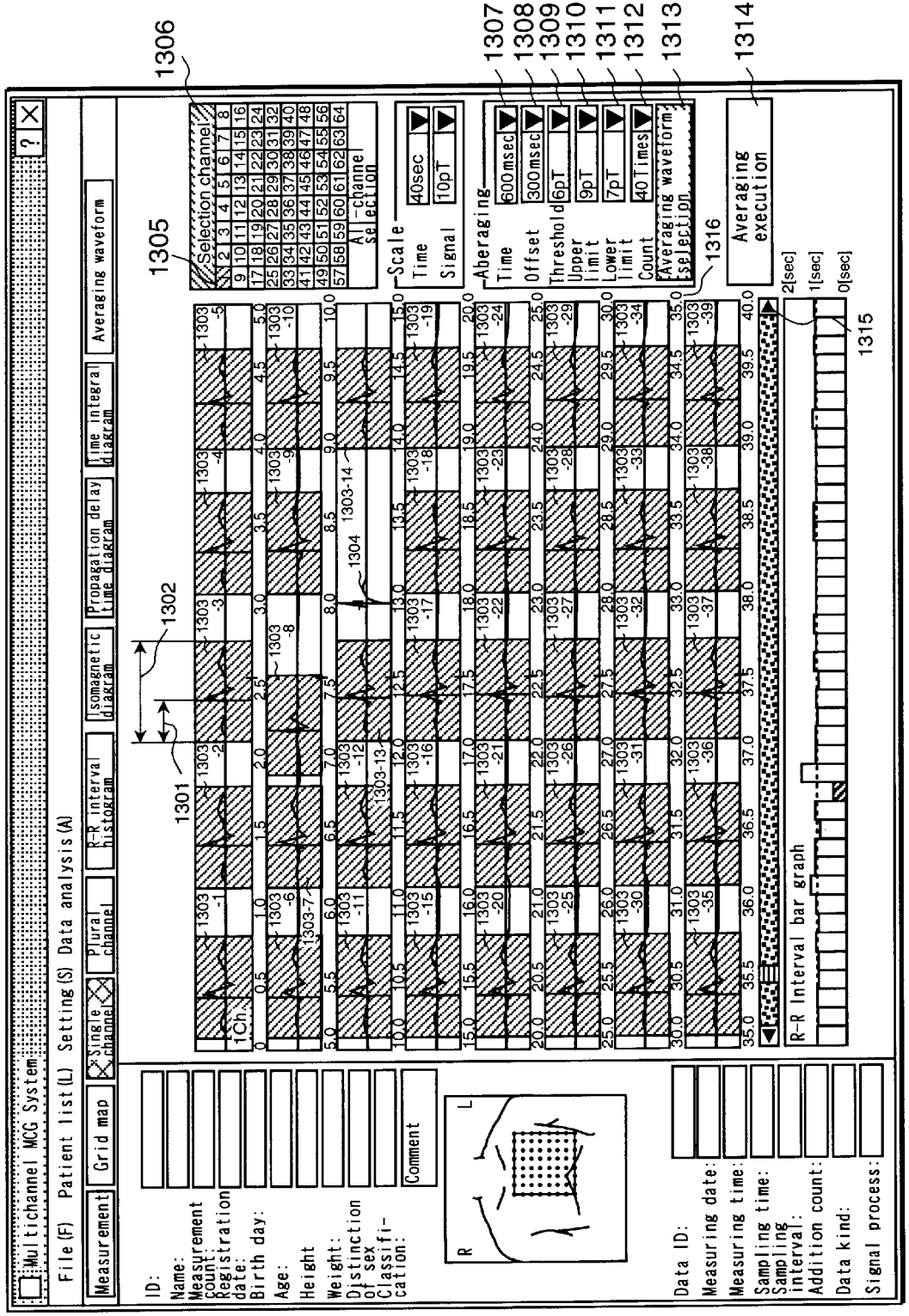
FIG. 15 shows a display screen selecting time waveforms fit to the averaging condition during the averaging process.
Figure 16:
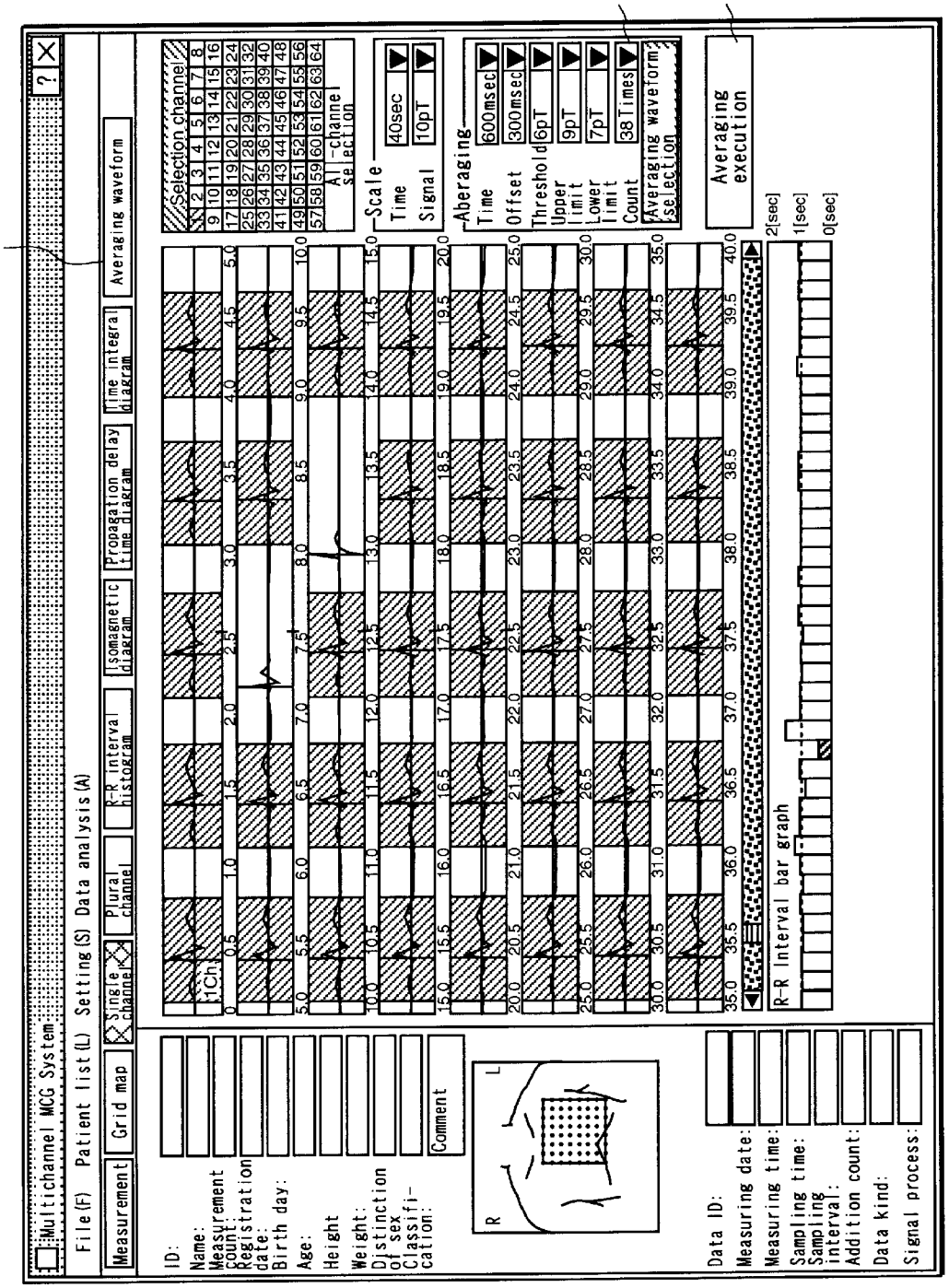
FIG. 16 shows a display screen selecting time waveforms fit to the averaging condition during the averaging process.
Figure 17:
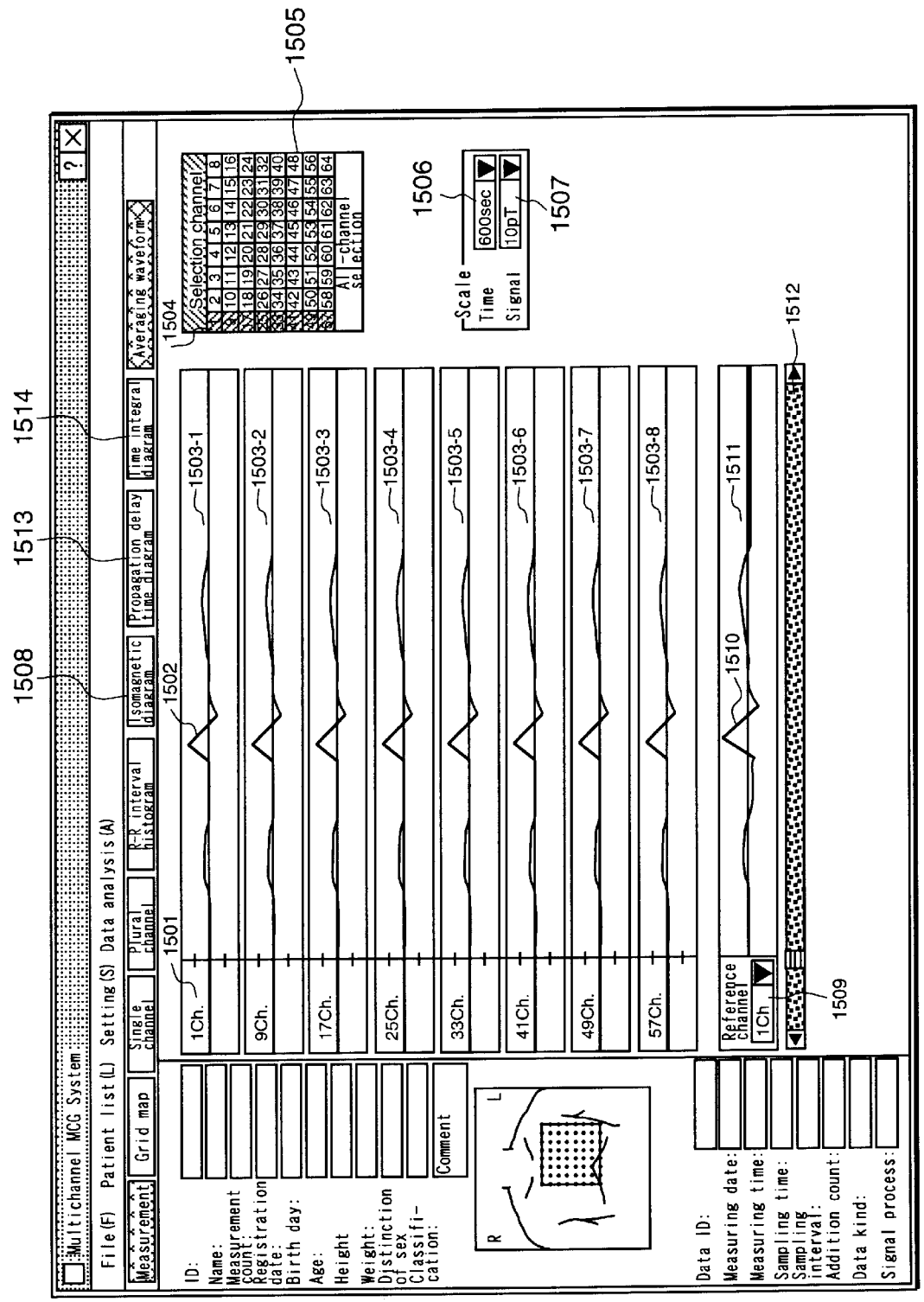
FIG. 17 shows a screen displaying time waveforms after the averaging process.
Figure 19:
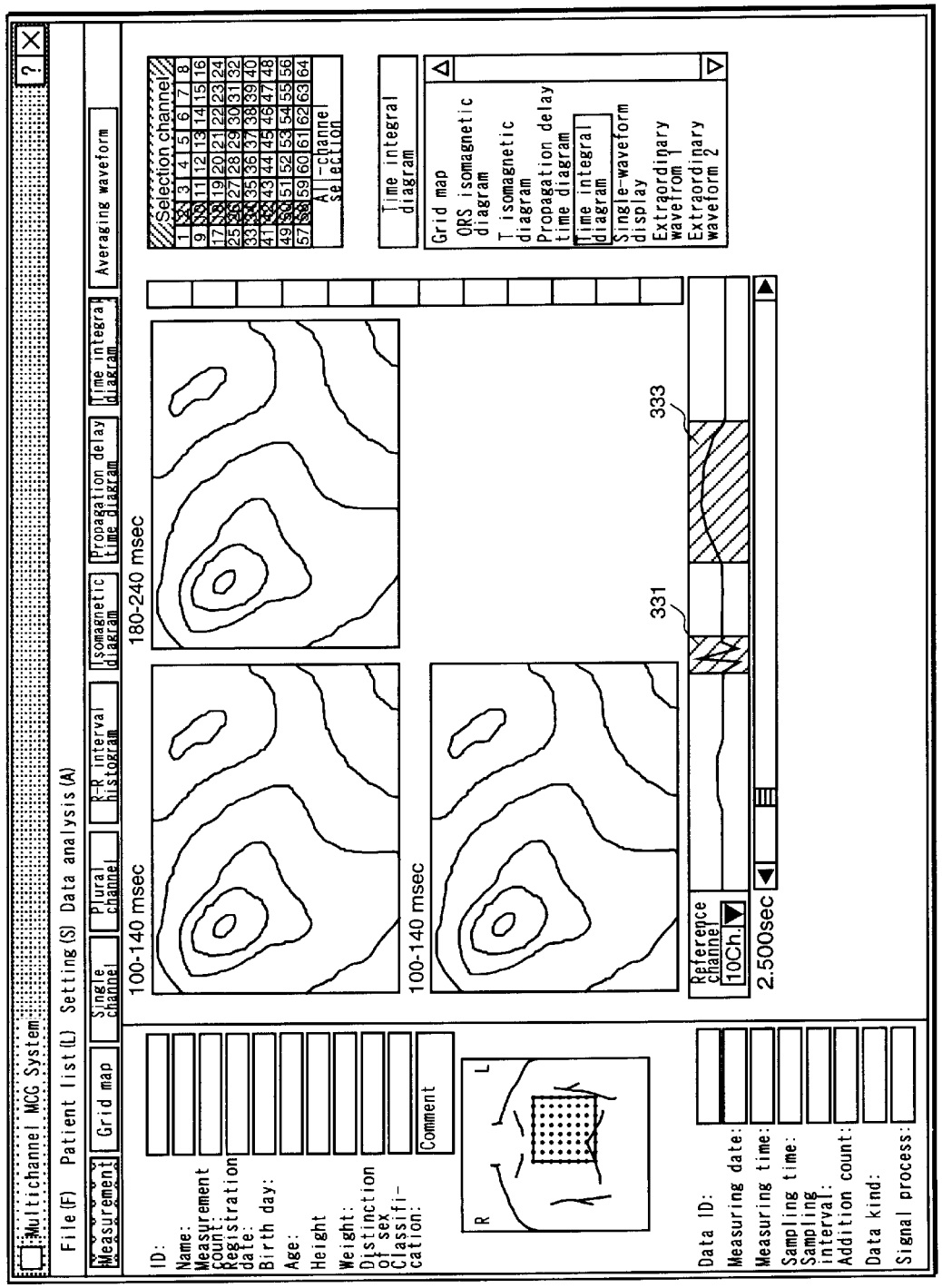
FIG. 19 shows a display screen example of a time integral diagram.

When the menu item "grid map display (G)" is selected in the "data analysis (A)" menu, the grid display screen shown in FIG. 8 is displayed. When the menu item "single channel waveform display (S)" is selected, a many-hour waveform of one channel is displayed as shown in FIG. 9. When the menu item "plural-channel waveform display (M)" is selected, a plural-channel many-hour waveform is displayed by dividing the screen horizontally as shown in FIG. 10 or 11. When the menu item "R-R interval display (R)" is selected, the RR interval histogram shown in FIG. 17 is displayed. When the menu item "averaging (V)" is selected, the averaging screens displayed in FIGS. 15 and 16 are displayed. When the menu item "isomagnetic diagram (C)" is selected, the isomagnetic diagram shown in FIG. 13 is displayed. When the menu item "propagation delay time diagram (P)" is selected, the "propagation delay time diagram (P)" shown in FIG. 14 is displayed. When the menu item "time integral diagram (T)" is selected, the time integral diagram shown in FIG. 19 is shown.

When "data measurement menu (Q)" is selected, the data measurement menu editing dialog shown in FIG. 7 is displayed and a menu registering data measurement condition is edited. The data measurement menu is a list menu of names (that is, data measurement protocol names) assigned to the parameter (measurement condition) values to be set for data measurement. On the left of the dialog, a text box 80 for designating a data measurement condition parameter is displayed; at the center, a data analysis menu 81-1 to be displayed after data measurement is displayed; and on the right, the data measurement condition list registered in the data measurement menu 82-1 is displayed.

In the data measurement condition parameters 80-1 to 80-7, set values such as the sampling interval, sampling time, input gain and output gain which are operation parameters of AFA6, high-pass filter, notch filter, and low-pass filter are provided and these values can be newly set and also added, deleted, or corrected.

Among them, in the sampling interval text box 80-1, the sampling interval is input from the keyboard in millisecond units and to provide easy input, a list of inputtable values is prepared. When the downward triangular button at the left end of the text box is pressed, the list is displayed and one of the values can be selected from the mouse. Other parameters also can be selected by pressing the triangular button in the same way and opening the list in which inputtable values are prepared.

The post-measurement display at the center designates the data analysis method to be displayed immediately after data measurement from the data analysis menu 81-1 registered already. In the data analysis menu 81-1, for the data analysis method such as the isomagnetic diagram and propagation delay time diagram, and the data analysis conditions (data analysis parameters) in which the parameters necessary for reconstruction of the aforementioned methods are designated, a list of names (discrimination information) set by an operator is displayed. The names can be freely set by the operator. However, a name indicating the object of data analysis and display content is generally used.

For example, in the example shown in FIG. 7, data menus such as the "grid map" displaying the time waveform in correspondence with the sensor position, the "QRS isomagnetic diagram" displaying the isomagnetic diagram of the QRS wave appearing by excitation of the cardiac ventricle, the "T isomagnetic diagram" displaying the isomagnetic diagram concerning the T wave in the same way, the "propagation delay time diagram" indicating the transfer time of a magnetic signal by contour lines, and the "time integral diagram" indicating the time integral value of the magnetic flux density at each sensor position by contour lines are registered, and among them, the "QRS isomagnetic diagram" is selected, and the selected one is displayed on the display unit 81.

In addition, in the data analysis menu, to provide an easy operation for diagnosis of a disease, for example, the menus of "P wave isomagnetic diagram", "irregular pulse waveform", and "RR interval" are added, and a display parameter for generating a P wave most suitable for diagnosis of the irregular pulse occurrence source and an equal magnetic diagram in the neighborhood thereof in correspondence to the "P wave equal magnetic diagram" is registered. Further, the display conditions of single-channel waveform display for catching the irregular pulse occurrence time at a glance for the "irregular pulse waveform" menu are registered, and the display conditions of RR interval display for detection of a heartbeat error due to the autonomic nerve for the "RR interval" menu may be registered.

Designation of post-measurement display is selected by designating the desired data analysis method from the data analysis menu 81-1 by the mouse. With respect to the name (discrimination information) of each list of the data analysis menu, the name of the diagnostic method can be assigned in place of the aforementioned. For example, when the contour line diagram of the QRS wave is considered to be valid in diagnosis of dilation of the heart, the display conditions of the equal magnetic diagram of the QRS wave may be registered in the name (discrimination information) of "cardiac hypertrophy diagnosis". When the difference in time integration between the QRS wave and the T wave is considered to be valid in diagnosis of myocardial ischemia in the same way, a contour line diagram of the integral values of the QRS wave and the T wave and the difference between the values may be registered in the name of "myocardial ischemia diagnosis". Namely, when such discrimination information is designated, the data analysis method (for example, grid analysis, QRS equal magnetic analysis, T equal magnetic analysis, propagation delay time analysis, etc.) preset in the dialog shown in FIG. 14 which will be described later and the data analysis condition parameters are read as a set and the desired data analysis process is performed after data measurement.

In the data measurement condition field at the right end, the data measurement condition name related to post-measurement display is designated. When the addition button 83-1 is pressed, the data measurement condition name text box 82 becomes empty and receives input of a data measurement condition name to be newly added. When the deletion button 83-2 is pressed, the item at the cursor in the data measurement condition list 82-1 is deleted. When the correction button 83-3 is pressed, the item at the cursor in the data measurement condition list 82-1 is displayed on the text box 82 and the contents thereof can be changed in consideration of the contents of the data measurement condition text boxes 80-1 to 80-7 and the post-measurement display designation unit 81.

The name (discrimination information) of the data measurement condition name may be assigned by the operator. However, generally, by setting the name indicating the measurement object, item, and method, measurement under an incorrect condition can be prevented.

In the example shown in FIG. 7, the names of "adult, front", "adult, back", "infant, front", "infant, back", and "unborn child" are registered and the name of "adult, front" is selected in the text box 82. When the discrimination information of "adult, front" is designated, the measurement conditions (parameters) of 0.5 milliseconds of sampling interval, 60 seconds of sampling time, input gain 10, output gain 50, and cut-off frequencies of 1 kHz, 50 Hz, and 0.01 Hz of the low-pass filter, band elimination filter, and high-pass filter are read and data measurement is executed according to the parameters (the aforementioned fourth embodiment of the present invention). Immediately after termination of the measurement, the data analysis method registered in the name of "QRS isomagnetic diagram" is executed according to the predetermined data analysis parameter and the result is displayed.

The magnitude of a magnetic signal to be measured is generally different between adult, infant, and unborn child and it is also different between measurement from the front and measurement from the back. The data analysis method for adult and infant mainly uses an isomagnetic diagram, though for unborn child, analysis by the time waveform is mainly used because the measuring direction and position are often unknown. By the "data measurement menu editing" dialog, even if an operator does not know the principle and structure of the equipment, he can operate the equipment easily by designating simple name discrimination information.

When the measurement start button 707 is pressed after these conditions are set, the measurement starts and a magnetic signal collected at a measuring time of 60 [s] and a sampling interval of 0.5 [ms] is stored in the magnetocardiograph raw data file 602 shown in FIG. 4.

When the data measurement is finished and post-measurement display is designated in the data measurement menu used for data measurement, the data analysis screen corresponding to it is displayed and when it is not designated, the patient list screen is displayed.

On the all-channel time waveform display screen shown in FIG. 8, in the all-channel time waveform display area 802, the time waveforms 801 of the collected magnetic signals corresponding to the channel numbers (indicated by the numeral 819) respectively are displayed and the waveforms of all the channels can be ascertained.

By changing the value of the time scale input box 805, the time of horizontal axis of the time waveform to be displayed in each time waveform display area 802 can be changed. In the same way, by changing the value of the signal scale input box 806, the amplitude of vertical axis of the time waveform to be displayed in the grid map time waveform display area 802 can be changed.

On the other hand, on the measurement screen shown in FIG. 5, when the single-channel time waveform display button 713-2 is pressed after measurement termination, the single-channel time waveform display processor 606 is selected by the display mode selection means 611 and the screen is switched to the single-channel time waveform display screen shown in FIG. 9. The time waveform display processor (time waveform display means) 606 displays the designated single-channel measurement signal on one screen across a plurality of lines of time axes as a time waveform.

On the single-channel time waveform display screen shown in FIG. 9, there is a selection channel area (channel display means) 906 on the upper right. As an example, the time waveform when channel No. 1 is selected by the channel button 905 is displayed in the waveform display area across a plurality of lines, and by the selection button 905, it is displayed by default so that selection of the corresponding channel can be visually checked. Also in the waveform display area, the selection channel display unit indicated by numeral 920 is set and 1 channel is displayed.

In the operation display area on the right of the screen shown in FIG. 9, 40 [s] is designated in the horizontal axis scale time box 908 of single-channel time waveform display and in the single-channel time waveform display areas 926-1 to 926-8 across a plurality of lines (8 lines in this case), the time waveforms (measured data) of 0 to 40 [s] are displayed. The horizontal axis scale time box 908 is a means for optionally setting the length of the time axis displaying the time waveform.

In the first row 926-1 of the single-channel time waveform display area, the time waveform 901-1 of 0 [s] to 5.0 [s] collected by one channel is displayed, and in the second row 926-2, the time waveform 901-2 of 5.0 [s] to 10.0 [s] is displayed. In the same way hereafter, the time waveforms up to the eighth row 926-8 are displayed in units of 5.0 [s].

When the maximum display time of the horizontal axis (time axis) of the single-channel waveform display is input to the time scale input box 908 of the time waveform horizontal axis, it can be changed to an optional display time width. According to this embodiment, the time waveform is measured at 60 [s], though 40 [s] is input to the time scale 908 and the time waveform for 40 [s] is displayed. To display a time waveform which is not displayed, it can be displayed by moving the horizontal axis scroll bar 925 provided on the lower part of the screen by operating the cursor by the mouse and keyboard. When 60 [s] is input to the horizontal axis scale time box 908, the time waveforms collected for the total time are displayed.

Also for the vertical axis scale, by inputting the maximum waveform width (maximum magnetic flux density) to the time waveform vertical axis scale width input box 909, the magnetic flux density can be changed to optional vertical axis magnetic flux density.

On the single-channel time waveform display screen shown in FIG. 9, when the plural-channel time waveform display button 929 of the menu bar unit is pressed (the plural-channel time waveform display button 929 shown in FIGS. 5 and 8 may be pressed) and the plural-channel time waveform display processor (time waveform display means) 607 is selected by the display mode selection means 611, the plural-channel time waveform display screen shown in FIG. 10 is output.

In FIG. 10, channel No. 1 (1007) and channel No. 4 (1007-2) are selected among the channel selection buttons of the selection channel area 1006. The time waveform display areas 1002-1 to 1002-4 and 1003-1 to 1003-4 are extended across 8 rows, so that the time waveforms 1001 of channel No. 1 are displayed in the upper four rows 1002-1 to 1002-4 and the time waveforms 1001-2 of channel No. 4 are displayed in the lower four rows 1003-1 to 1003-4. In this embodiment, the time waveforms of channel Nos. 1 and 4 are selected. However, the channel number can be selected optionally by the channel selection button 1006 and the time waveform of the selected channel number is displayed.

FIG. 11 shows the time waveforms of four channels on the plural-channel time waveform display screen. In this example, channel Nos. 1, 4, 40, and 56 are selected by the selection button of the selection channel area (channel display means) 1101, so that they are displayed in the time waveform display areas 1104-1 and 1104-2, 1105-1 and 1105-2, 1106-1 and 1106-2, and 1107-1 and 1107-2 every two rows. The time waveforms 1101-1 of channel No. 1 are displayed in the time waveform display areas 1104-1 and 1104-2; the time waveforms 1101-2 of channel No. 4 are displayed in the time waveform display areas 1105-1 and 1105-2; the time waveforms 1101-3 of channel No. 40 are displayed in the time waveform display areas 1106-1 and 1106-2; and the time waveforms 1101-4 of channel No. 56 are displayed in the time waveform display areas 1107-1 and 1107-2. The time waveform display areas on the plural-channel time waveform display screen are extended across 8 rows, so that up to 8 channels can be designated at one time.

On the single-channel time waveform display screen shown in FIG. 9, when the pointing device (one-point display means) is pointed onto the time waveforms 901-1 to 901-8 like 918 by mouse operation, the magnetic flux density corresponding to the time of the point of the time waveform is displayed like 919. By doing this, the accurate magnetic flux density and time at an optional point on the time waveforms 901-1 to 901-8 can be ascertained.

On the lower part of the single-channel time waveform display screen shown in FIG. 9, a bar graph display area 927 of the R-R interval (peak interval) which is the time interval (called R-R interval) from the maximum (peak value of the R wave) of each heartbeat of the collected magnetocardiograph waveforms to the maximum of the next heartbeat is provided. The R-R interval bar graph display area 927 is displayed on the screen shown in FIG. 9 by selecting the R-R interval histogram display processor (bar graph display means) 608 by the display mode selection means 611 in the single-channel time waveform display mode. The horizontal axis of the display area 611 shows the R-R intervals in the collection order and the vertical axis 923 indicates the R-R interval time, and hence each R-R interval is indicated by a bar graph 921.

The R-R interval bar graph 921 shows that the time interval of heartbeats of the heart of a human is generally almost constant and it is a guideline for finding a signal when the R-R interval is decreased or increased than the normal interval due to high or low running of the feeling of a patient or noise other than the magnetocardiograph field enters by any disturbance.

According to this embodiment, a signal waveform 904 which seems to be disturbance enters in the neighborhood of about 13 seconds and numeral 922 indicates it in the R-R interval bar graph 921. In this case, the signal waveform 904 which seems to be disturbance is not subjected to the averaging process (this will be described later).

When it is required to know the interval of what waveform of the time waveforms is displayed by each bar graph on the R-R interval bar graph display unit 927, if the R-R interval bar graph to be known is designated by the cursor, in the designated bar graph and the area of the R-R interval (peak interval) corresponding to it in the time waveform, it is coated with a discrimination (color or shading in place of color) which is discriminated from other time waveforms and displayed. In this embodiment, the state that the bar graph 922 is pressed, a discrimination color is coated in the corresponding waveform area 926, and the waveform is displayed is shown.

Figure 12:
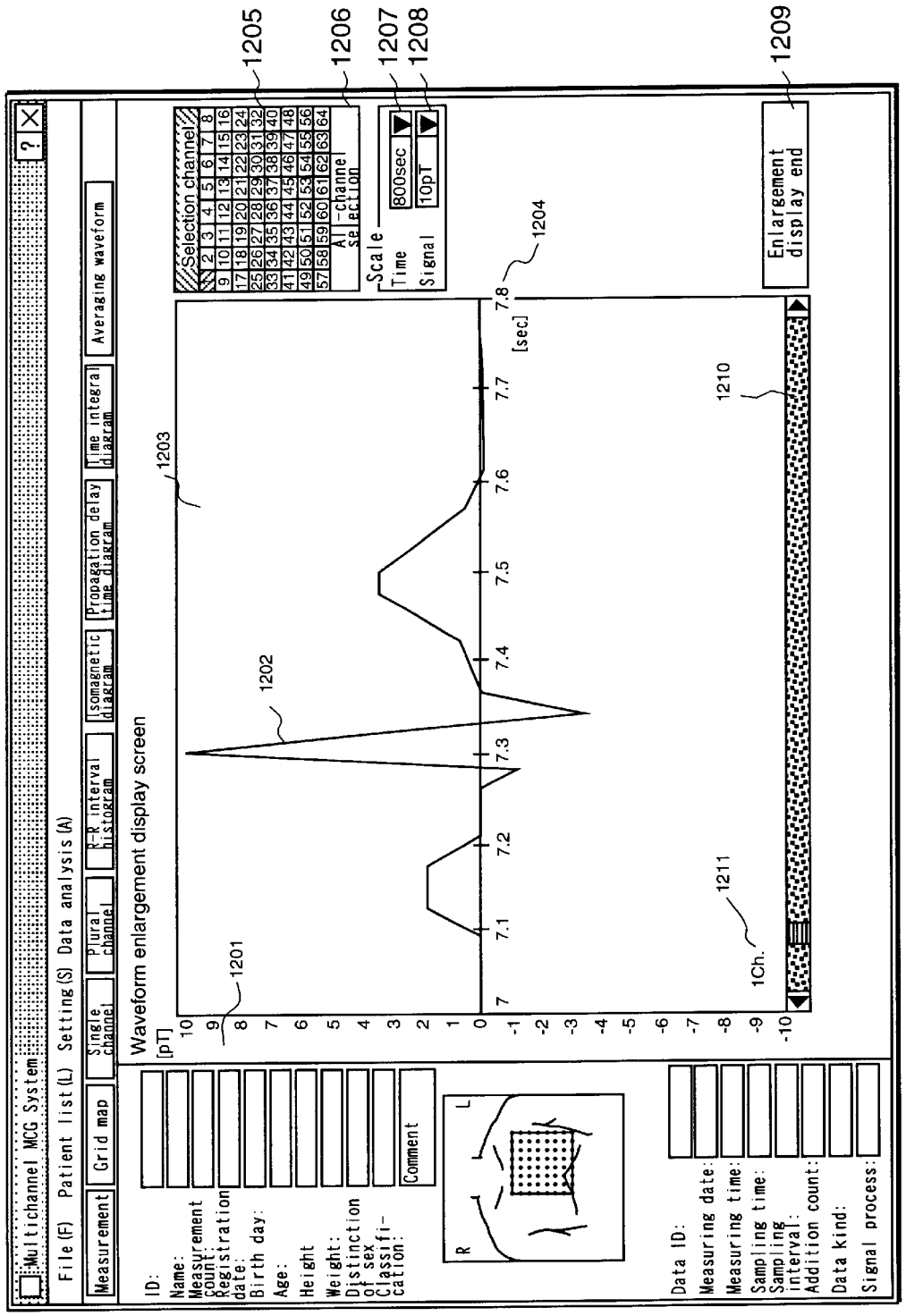
FIG. 12 shows an enlarged waveform display screen example.

In the single-channel time waveform display areas 926-1 to 926-8 shown in FIG. 9, when the area is selected by the pointing device such as the mouse as shown by 902 and the waveform enlargement button 928 in the operation display area is pressed, the time waveform enlargement display processor (waveform enlargement display means) 605 is selected by the display mode selection means 611, the screen is switched to the enlargement waveform display screen shown in FIG. 12 by the time waveform enlargement display processor 605, the waveform in the selected area 902 is enlarged, and the time waveform (heartbeat waveform) 1202 is displayed in the enlargement time waveform display area 1203. The vertical axis 1201 indicates the scale of the magnetic flux density of the magnetocardiograph field and the horizontal axis 1204 indicates the time scale.

The time scale of the horizontal axis 1201 is 800 [ms] of the horizontal axis selection range designated by the default 902 (see FIG. 9). However, by inputting an optional time to the scale time input box 1207 in the operation display area on the right of the screen, it can be changed to an optional scale width. Also in the vertical axis scale, by inputting the maximum magnetic flux density to the vertical axis scale width input box 1208 of time waveform, it can be changed to optional vertical axis magnetic flux density (maximum vertical width of waveform).

By moving the horizontal axis time waveform scroll bar 1210 right and left, the time waveform in time can be seen in other than the enlargement time waveform display area.

When the enlargement display end button 1209 is pressed, the enlargement waveform display screen shown in FIG. 12 is preset to finish and return to the screen previously displayed.

On the single-channel time waveform display screen shown in FIG. 9, when an area is selected by the pointing device such as the mouse as shown by numeral 902 in the single-channel time waveform display areas 926-1 to 926-8 and the isomagnetic diagram display button 917 is pressed, the isomagnetic diagram display processor 609 is selected by the display mode selection means 611 and the screen is switched to the isomagnetic diagram display screen shown in FIG. 13.

By the isomagnetic diagram display processor 609, the time waveform 926 within the range selected by the pointing device 902 is displayed in the reference channel display area 1605 and the isomagnetic diagram 1601 of the time waveform 926 at the first time is displayed by default. By the isomagnetic diagram display time setting cursor 1603 or by inputting the time to be displayed to the isomagnetic diagram display time input box 1609, an isomagnetic diagram at an optional time is displayed. By moving the time waveform scroll bar 1606 right and left, a time waveform which is not displayed in the reference channel display area 1605 is displayed.

When "Data analysis menu (B)" shown in FIG. 6 is selected, the dialog shown in FIG. 14 is opened and receives the data analysis menu editing operation. On the upper part of the dialog, a standard magnetocardiograph model waveform is displayed and the start times of the P wave, T wave, and U wave and the times when the QRS wave is maximized and minimized are displayed with symbols TP, TQ, TR, TS, TT, and TU assigned respectively. On the lower left of the dialog, there is an area for inputting the data analysis method and parameters necessary for it and on the lower right, the data analysis menu to be edited is arranged. In the example shown in FIG. 11, "Grid map", "QRS isomagnetic diagram", "T isomagnetic diagram", "Propagation delay time diagram", and "Time integral diagram" are registered and "QRS isomagnetic diagram" is selected. The data analysis method of "QRS isomagnetic diagram" displays isomagnetic diagrams at the five times of TQ−10, TQ, TR, TS, and TS+10. These times are indicated by dashed lines in the time waveform displayed on the upper part of FIG. 14 as shown by numeral 90-2.

When the addition button 104-1 is pressed, the data analysis name input from the text box 105 on the upper part of the data analysis menu 105-1 is added to the menu. When the deletion button 104-2 is pressed, the item at the cursor in the data analysis menu is deleted. When the correction button 104-3 is pressed, the content of the item at the cursor is set in the data analysis condition unit on the left and the content can be changed.

The data analysis kind which can be set from the data analysis condition unit is grid map, isomagnetic diagram, time integral diagram, and propagation delay time diagram, designated by the radio button on the left. To the text boxes provided on the right of the isomagnetic diagram, time integral diagram, and propagation delay time diagram, the time constituting the isomagnetic diagram, the time for executing time integration, and the reference time for obtaining the propagation delay time are input respectively.

The time for reconstituting the isomagnetic diagram is designated by setting the time TR of the R wave automatically detected as "TR, TR+2, TR+4, - - - " as a parameter and adding or subtracting the time difference from it. When reconstituting the isomagnetic diagram at a plurality of times, it is desirable to enumerate by delimiting with commas (,) in the desired number.

For the time for executing time integration, the time integration from the S wave to the Q wave is designated like (TS, TQ). When two sections are to be integrated like the QRS wave time integration and T wave time integration, it is desirable to enumerate sequentially the first time and last time of the integration section like "TS, TQ, TT, TT+100". According to this embodiment, when two integration sections are designated, two time integral diagrams and a map of the difference between their integral values are displayed. For the reference time of the propagation delay time, one time is designated.

Next, the averaging process of measured data (waveform of magnetocardiograph) will be explained. The averaging process is to fetch a signal waveform of one heartbeat repeatedly appearing from a measurement signal for each channel for measurement signals from the magnetic sensors of all the channels, and add and average the heartbeat data (signal waveform) by the designated addition count.

Assuming noise overlapped with a magnetocardiograph signal and fetched during data measurement by performing the averaging process as white noise, the noise level can be reduced to 1/(square root of addition count), so that the ratio of signal to noise can be improved. Even in a disease such as myocardial ischemia or cardiac hypertrophy whose subjective symptom does not appear in a patient himself, there is the possibility that he can be diagnosed by preparing an isomagnetic diagram from averaged signals.

For signal data of one heartbeat, a method for detecting the R wave by shape recognition of the threshold value and waveform and setting the point of time after a fixed time from the time as an averaging start time is used.

In this embodiment, there are a method for displaying the time waveforms of magnetocardiograph measured data on the screen and adding and averaging data by ascertaining each heartbeat waveform and a method for recognizing the waveform of one heartbeat immediately after data measurement and automatically adding and averaging data. The methods will be explained hereunder.

The averaging process is performed by the averaging means (calculation means) 603 by setting conditions in the averaging condition setting input box in each operation display area on the all-channel time waveform display screen shown in FIG. 8, the single-channel time waveform display screen shown in FIG. 9, and the plural-channel time waveform display screen shown in FIG. 10, Here, the averaging process on the single-channel time waveform display screen will be explained first.

On the single-channel time waveform display screen shown in FIG. 9, the parameters indicated in the averaging condition setting input box arranged on the right are parameters for execution of the averaging process.

Among the parameters, for the threshold value 912, the value of the magnitude of the magnetic flux density of one heartbeat is input, the upper limit 913 and lower limit 914 designate the magnetic flux density range for finding the maximum R wave of one heartbeat, and the offset time 1301 (see FIG. 15) designates the time before the time corresponding to the threshold value 913 when the averaging process is to be performed in the waveform in which the maximum R wave of one heartbeat exists between the lower limit value 914 and the upper limit value 913 within one heartbeat and is input to the offset input box 911.

The averaging time is the whole time for performing the averaging process and input to the averaging time input box 910. According to this embodiment, the averaging process is performed by inputting 800 [ms] to the averaging time input box 910, 400 [ms] to the offset time input box 911, 6 [pT] to the threshold value input box 912, 9 [pT] to the upper limit 913, and 7 [pT] to the lower limit 914.

When the averaging waveform selection button 916 of the menu bar is pressed after the aforementioned averaging conditions (parameters) are set, the screen is switched to the screen shown in FIG. 15, the waveforms coinciding with the averaging parameters (waveforms satisfying the averaging conditions) are coated and displayed with discrimination colors showing coincidence as shown by 1303-1 to 1303-39, and the waveforms with the discrimination colors coated are waveforms to be averaged.

The waveform indicated by numeral 1304 has a maximum amplitude of about 10 [pT] and it is beyond the range of 9 [pT] input to the upper limit input box 1310 and 7 [pT] input to the lower limit input box 1311, so that the waveform is not an averaging object.

The averaging count is the number of waveforms to be averaged and displayed on the averaging count input box 1312.

Figure 18:
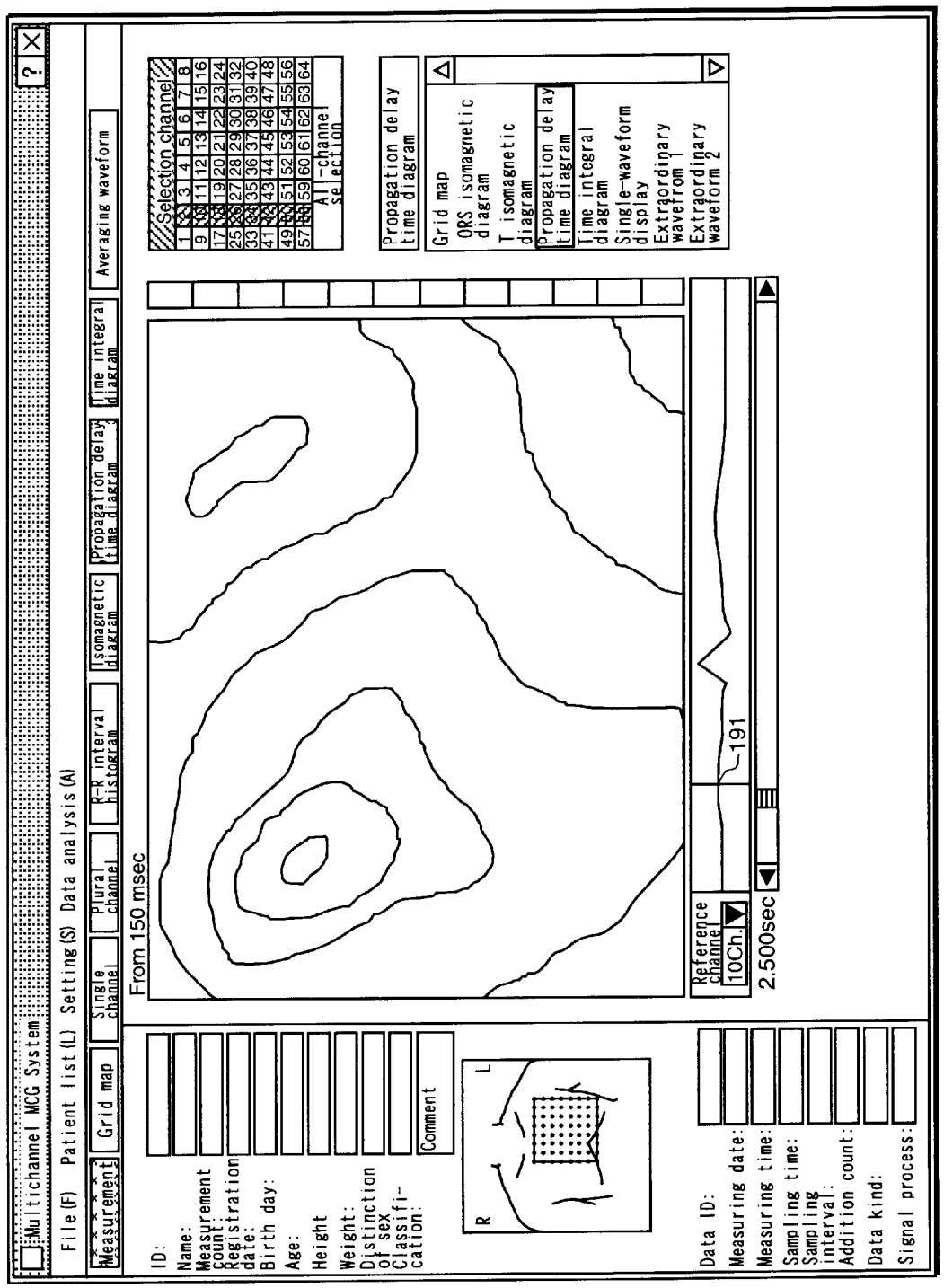
FIG. 18 shows a display screen example of a propagation delay time diagram.

With respect to selection of averaging waveforms, in addition to the method for selecting by setting and calculating averaging conditions as mentioned above, they can also be optionally and directly selected by an operator via the screen. When the area where the heartbeats not to be averaged are selected in the waveforms selected by 1303-1 to 1303-39 is pressed, the colors are erased and the waveforms will not be averaged. On the other hand, when one of the unselected waveforms (heartbeats) is designated and clicked by the cursor, the range across before and after the clicked place is discriminated and displayed as a selected range. According to this embodiment, the heartbeat waveform 1303-8 to be averaged is clicked and is not averaged as shown in FIG. 18. The number of heartbeat waveforms to be averaged is reduced by one and the averaging count 1401 is displayed as 38 times. The averaging waveform selection means may be composed of only one of the method for selecting the time waveform satisfying the averaging conditions by calculation and the method for directly selecting by an operator via the screen as mentioned above.

When the averaging execution button 1402 is pressed, the selected heartbeat waveforms are averaged. In this case, also for the other channels, the waveforms are averaged at the same time as that of the waveform selected in FIG. 18. Namely, even in the other channels, the waveforms not to be averaged are the same, so that the waveforms are averaged at the same time as that of the waveforms displayed on the screen.

The results of the averaging process are stored in the magnetocardiograph averaging data file 604 shown in FIG. 4. When the averaging waveform display button 1403 is pressed, the screen is switched to the averaging waveform display screen shown in FIG. 17.

On the other hand, to automatically execute the averaging process immediately after data measurement, the menu item "Automatic averaging (V)" in the "Setting (S)" menu is selected, the automatic averaging condition dialog shown in FIG. 10 is opened, and the conditions are set. For the reference channel, the channel for deciding the time section for the adding process is designated. Namely, on the reference channel, the peak time TR of the R wave is detected, and the start time of heartbeat waveforms to be averaged is decided on the basis of it. Furthermore, the signal data from the start time to the time added with the averaging time is set as heartbeat data. The time section for performing the averaging process which is decided here is commonly used for the other channels. The addition count indicates the number of heartbeat waveforms when the addition process is performed. The value input by an operator is decided by the [OK] button and the dialog is closed, and the value input by the [Cancel] button is discarded and the dialog is closed.

On the averaging waveform display screen shown in FIG. 17, in the averaging waveform display areas 1503-1 to 1503-8, the time waveforms for which the averaging process is performed are displayed. The channel number of the time waveform to be displayed can be optionally selected by operating the button of the selection channel (channel display means) 1505. According to this embodiment, the channel numbers 1, 9, 17, 25, 33, 41, 49, and 57 indicated by 1504 are selected; in the averaging waveform display area 1503-1, the waveform 1502-1 of channel No. 1 is displayed; in the averaging waveform display area 1503-2, the waveform 1502-2 of channel No. 9 is displayed; and in the same way hereinafter, the waveforms up to channel No. 57 are displayed.

The horizontal axis time scale 1506 and the vertical axis magnetic flux density scale 1507 can be changed by inputting an optional value. By moving the horizontal axis scroll bar 1512 right and left, the time which is not displayed is displayed.

When the isomagnetic diagram display button 1508 is pressed, the screen is switched to the isomagnetic diagram screen shown in FIG. 13. When the propagation delay time diagram display button 1513 is pressed, the screen is switched to the propagation delay time diagram shown in FIG. 18. When the time integral diagram display button 1514 is pressed, the screen is switched to the time integral diagram shown in FIG. 19.

On the isomagnetic diagram display screen shown in FIG. 13, in the time waveform display area 1605, the averaging waveform 1510 displayed before this screen is opened is displayed. By inputting the channel of the waveform to be displayed in the time waveform display area 1605 by the reference channel input box, the time waveform at an optional channel can be displayed. In the isomagnetic diagram display area 1601, the isomagnetic diagram at the designated time by the display time input box 1609 is displayed. The display time designation cursor 1603 is displayed at the position of the time corresponding to the display time input box 1609.

On the propagation delay time diagram display screen shown in FIG. 18, according to this embodiment, another data analysis menu is provided on the left of the screen. However, a text box for inputting the reference time for deciding the time up to the R wave may be provided. The propagation delay time is the time from the reference time to the R wave which is mapped.

Also on the time integral diagram display screen shown in FIG. 19, according to this embodiment, another data analysis menu is provided on the left of the screen. However, display parameters for preparing a time integral diagram, that is, a text box for setting the maximum value of time integration for deciding colors necessary for preparing an isomagnetic diagram of the integration time section or time integral value and the contour line interval, may be provided.

Figure 20:
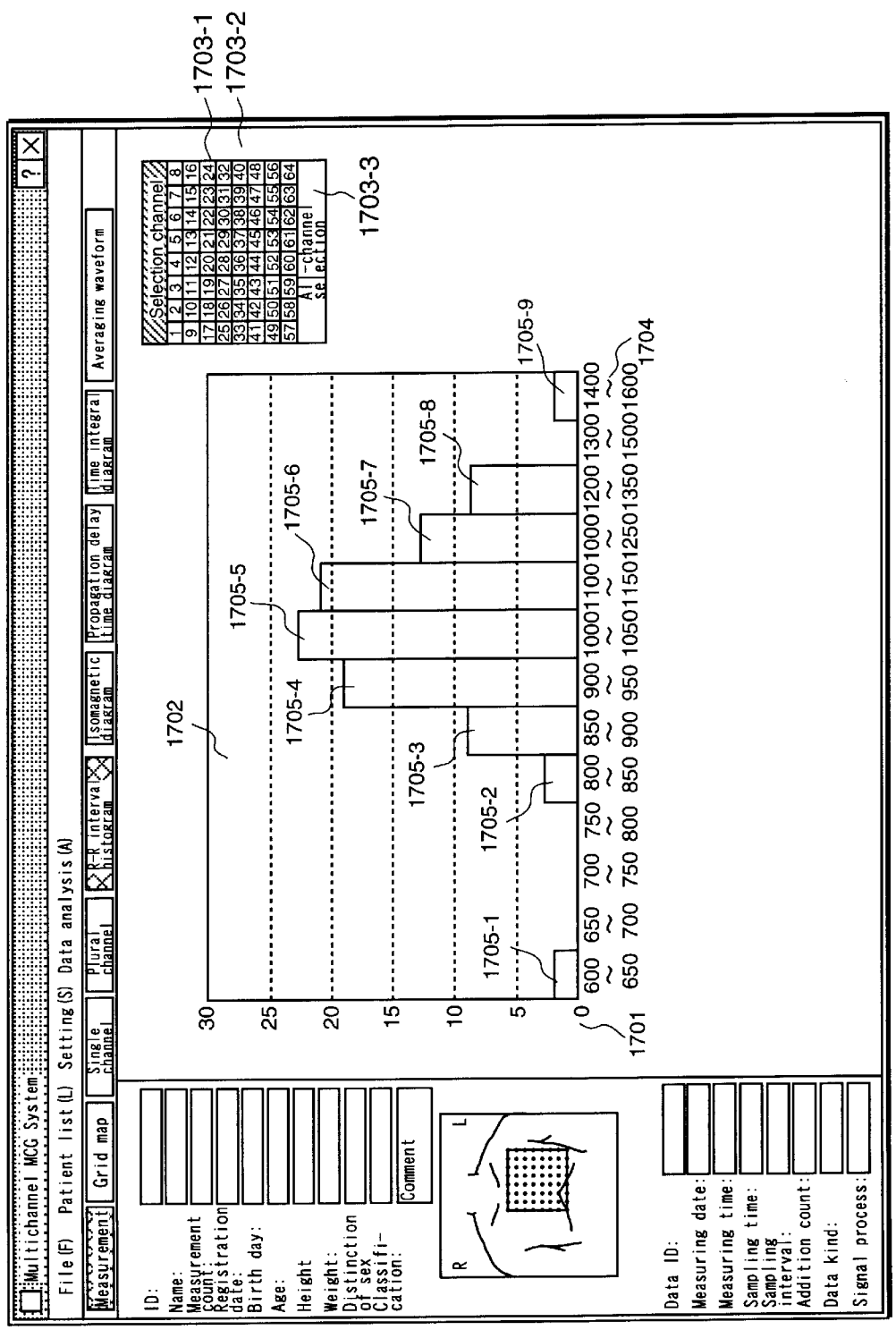
FIG. 20 shows a display screen example after the R-R interval histogram display process is performed.

When the R-R interval histogram display button is pressed, the R-R interval histogram display screen shown in FIG. 20 is displayed by the R-R interval histogram display processor 608. According to this embodiment, the histogram of the time waveform of channel No. 37 (1703-2) designated by the button of the selection channel (channel display means) 1703-1 is displayed. The frequency of the R-R interval time is calculated at an interval of 50 [ms] starting from 600 [ms], the horizontal axis is indicated by the R-R interval time at an interval of 50 [ms], and the vertical axis is displayed as frequency in the R-R interval histogram display area 1702. According to this embodiment, a histogram of one channel is displayed. However, as objective channels, histograms can be displayed also for a plurality of channels designated by the selection channel 1703-1.

When "Automatic averaging condition (A)" shown in FIG. 6 is clicked, the "automatic averaging condition" dialog box shown in FIG. 21 is displayed and receives the reference channel number of the magnetic sensor designated by an operator, start time, averaging time, and addition count.

On the left of the dialog shown in FIG. 21, a standard magnetocardiograph model waveform is displayed and the starting times of the P wave, T wave, and U wave are displayed by assigned symbols TP, TT, and TU (numeral 90 indicates a magnetocardiograph waveform and 91 a zero line). The times of the QRS wave at the maximum point and minimum point of each wave are assigned TQ, TR, and TS respectively. According to the present invention, these times are automatically decided for the waveforms of the reference channel. An example of the decision method for these times is such that for example, TR is decided by detection of the R wave, and on the basis of TR, the time at the minimum point immediately after is set to TS, and the time at which the signal of T wave rises after signals of the 0 level are continued for more than the fixed time is set to TT. In the same way, TP, TQ, and TU can be decided. TP, TT, and TU may be defined as times for providing the maximum points or minimum points of the P wave, T wave, and U wave respectively. In this case, for example, to decide TP, the time at which the signal value is maximized between (TR-300) ms and (TR-150) ms is set to TP, and TT and TU are decided in the same way.

On the right of the dialog, text boxes 92, 93, 94, and 95 for inputting the reference channel, start time, averaging time, and addition count are provided. Depending on the position of each magnetic sensor, the signal waveform of each channel is reversed in polarity and the time for giving the TR is shifted, so that to decide the time range of one heartbeat, it is necessary to set the reference channel from the magnetic sensors, and one channel number is designated from the channel Nos. 1 to 64 by the reference channel text box 92. When the chest of an adult is measured from the front, channel 8 corresponding to the magnetic sensor at the 8th column of the first row where the amplitude is large, and the R wave is easily detected, is generally designated.

In the start time text box 93, the averaging start time is designated by the relative time from the start times TP, TQ, TT, and TU of the P wave, T wave, and U wave. In the example "TR-300" shown in FIG. 21, the time TR (the time corresponding to the turning value of the R wave) of the R wave is detected from the magnetic field waveform of the reference channel and the point of time 300 ms before the time is set to the averaging start time. It indicates the time before the time TP when the P wave of a healthy person is generated and the averaging time 800 ms is a time sufficiently long to fully cover the time from occurrence of the P wave to its end. Namely, the example shown in FIG. 21 identifies the time TR corresponding to one point of the characteristic wave repeatedly appearing by the physiological activity from the measured signal waveform and extracts the signal waveform within the time range decided on the basis of this time as physiological magnetic field analysis data (the third embodiment of the present invention mentioned above). Generally, when the equipment indicated by the present invention is used for diagnosis, the starting time is set within the range from TR-250 to TR-300 or so and the averaging time is set within the range from 750 to 800 ms or so. When the interval from the P wave to the QRS wave is long and the waveform of the P wave is to be surely averaged, if "TP-50" is described in the same way, the time 50 ms before the top of the P wave can be set to the averaging start time.

In the averaging time text box 94, the length of a magnetocardiograph signal of one heartbeat obtained as a result of averaging is designated in units of ms. In the addition count text box 95, the addition count for averaging is designated.

These designations become valid when the OK button 96 is pressed and the dialog shown in FIG. 21 is closed. When the cancel button 97 is pressed, the information set in the text box becomes invalid and the dialog is closed.

Figure 22:
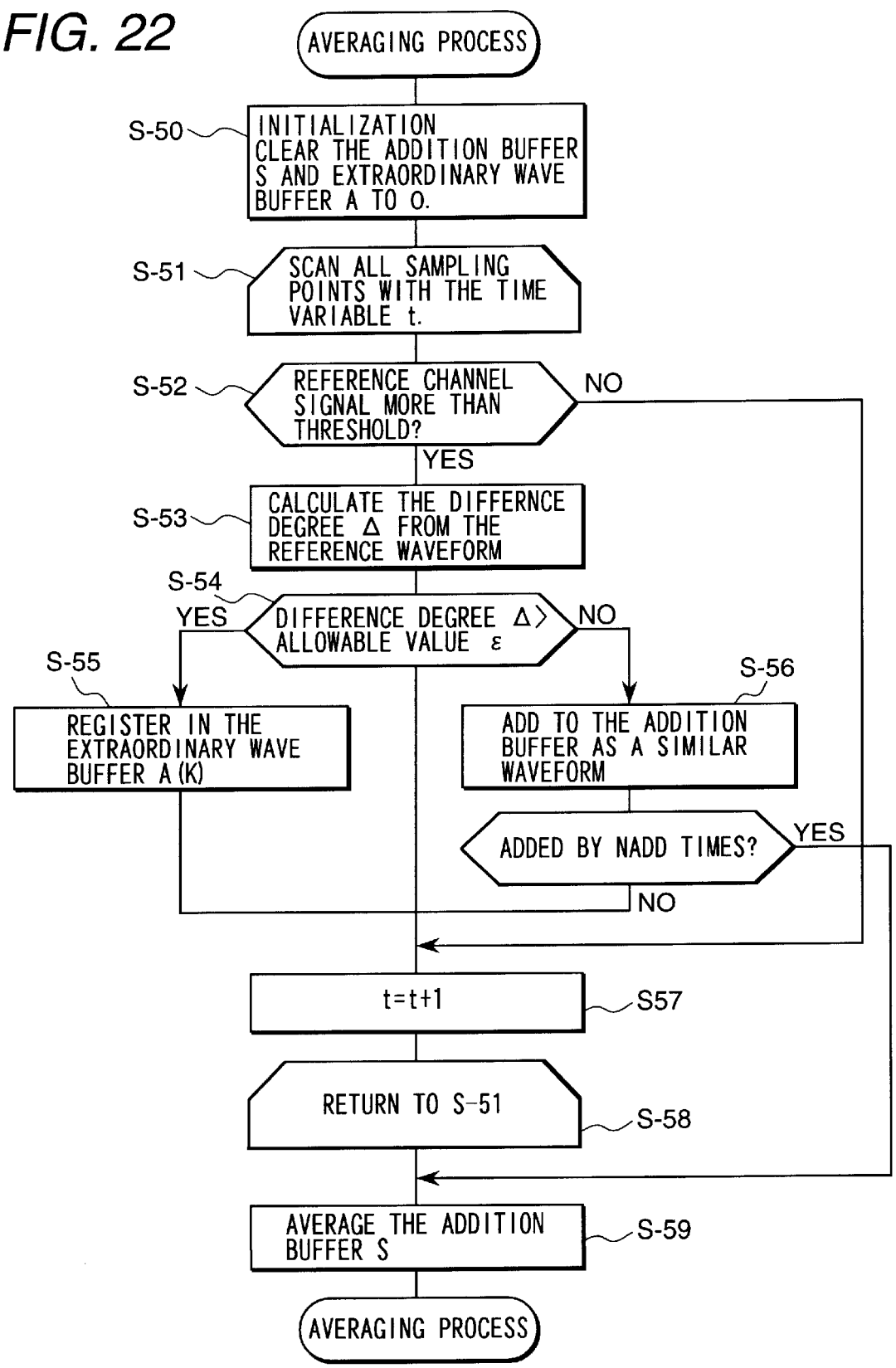
FIG. 22 is a drawing showing the flow of the averaging process.

FIG. 22 shows a flow chart for executing automatic averaging and abnormal data registration relating to the first and second embodiments of the present invention.

In FIG. 22, firstly, as the initialization process S-50, the addition buffer S and the extraordinary buffer A are cleared to zero. From Step S-51, a repetitive process (loop) starts, for scanning all the sampling points of measurement data from the time 0 using the time variable t.

At the time t, whether the signal value of the reference channel exceeds the threshold value for detecting (waveform recognition) the R wave (signal waveform) or not is decided (S-51, waveform recognition means) and when it is NO, the program goes to Step S-57 and the process at the next time is performed. When it is YES, the time TR of the R wave is decided and the difference degree Δ between the signal waveform at the preceding and subsequent times designated at Step S-53 and the reference waveform is obtained (S-53, waveform evaluation means, setting of the reference waveform will be described later).

The difference degree Δ is an amount indicating the difference between the signal waveform X of one heartbeat which is intended to add to the addition buffer and the reference waveform Y registered already. As a concrete definition of the difference degree Δ, there is a total of square errors of the waveform at the time corresponding to the signal waveform X at all the channels and the reference waveform Y. Assuming the number of sampling points of signal data of one heartbeat as T, the number of sampling points from the top as n, and the channel number as m, the difference degree Δ is expressed as follows:

Formula 1

$$\Delta = \sum_{m=1}^{64} \sum_{n=1}^{T} |X_{m,n} - Y_{m,n}|^2$$

Formula 1

The effects of an irregular pulse which is a difference between the signal waveform X and the reference waveform Y and external magnetic field noise can be seen commonly in all the channels, so that the square error of only the reference channel may be defined as a common difference degree Δ of each channel. Furthermore, the difference in the occurrence time between the P wave, QRS wave, T wave, and U wave and the difference in the signal intensity may be calculated and used as a difference degree Δ.

The difference degree Δ is compared with the allowance ε which is incorporated in the equipment (program) beforehand at the next step S-54, and when the difference degree Δ is larger, the signal data X of one heartbeat is registered in the extraordinary wave buffer A (S-55, waveform registration means). When the difference degree Δ is smaller, the signal data X is added to the addition buffer as a similar waveform of the reference waveform, and the addition count is incremented only by one (S-56). When the addition count reaches the designated count Nadd with the result that the addition count is incremented, the program gets out of the loop of time variable and goes to Step S-59. When the addition count does not reach the addition count Nadd, the program goes to Step S-57 and repeats the same processing. After the program gets out of the loop of the time variable t, the program divides by the signal value Nadd of the addition buffer and obtains an average value (S-59) and the averaging process is finished. Namely, S-56 to S-59 are averaging process calculation means of the calculator 8.

As an example of the reference waveform Y setting method, there is a method available for registering the part of measured data equivalent to the first heartbeat during the initial process of S-50 in the reference waveform registration means as a reference waveform Y (not only the first heartbeat but also the heartbeat of any turn may be selected). According to this method, regular heartbeat data is not always registered as a reference waveform but may include an irregular pulse or external magnetic field noise. However, these waveforms do not coincide with the subsequent heartbeat data, so that the addition is not executed by the predetermined count and the averaging process terminates abnormally. After the end of measurement, an operator can detect the error immediately and execute the measurement again. Alternatively, he may reselect the reference wave, execute the flow shown in FIG. 22 again, and perform the averaging process.

As another example, there is a method available for providing an item of "Reference waveform registration" in "Data measurement menu (Q)" shown in FIG. 6 (not shown in the drawing), fetching the waveform of one heartbeat on the waveforms frozen on the screen when the item "Reference waveform registration" is selected in the state that the monitor [OFF] button of the measurement monitor 157 shown in FIG. 16 is pressed, and registering it after checking whether it is suited as a reference waveform on the screen. There are other checking methods available such as displaying of a checking dialog or installing of a checking button on the screen.

Figure 23:
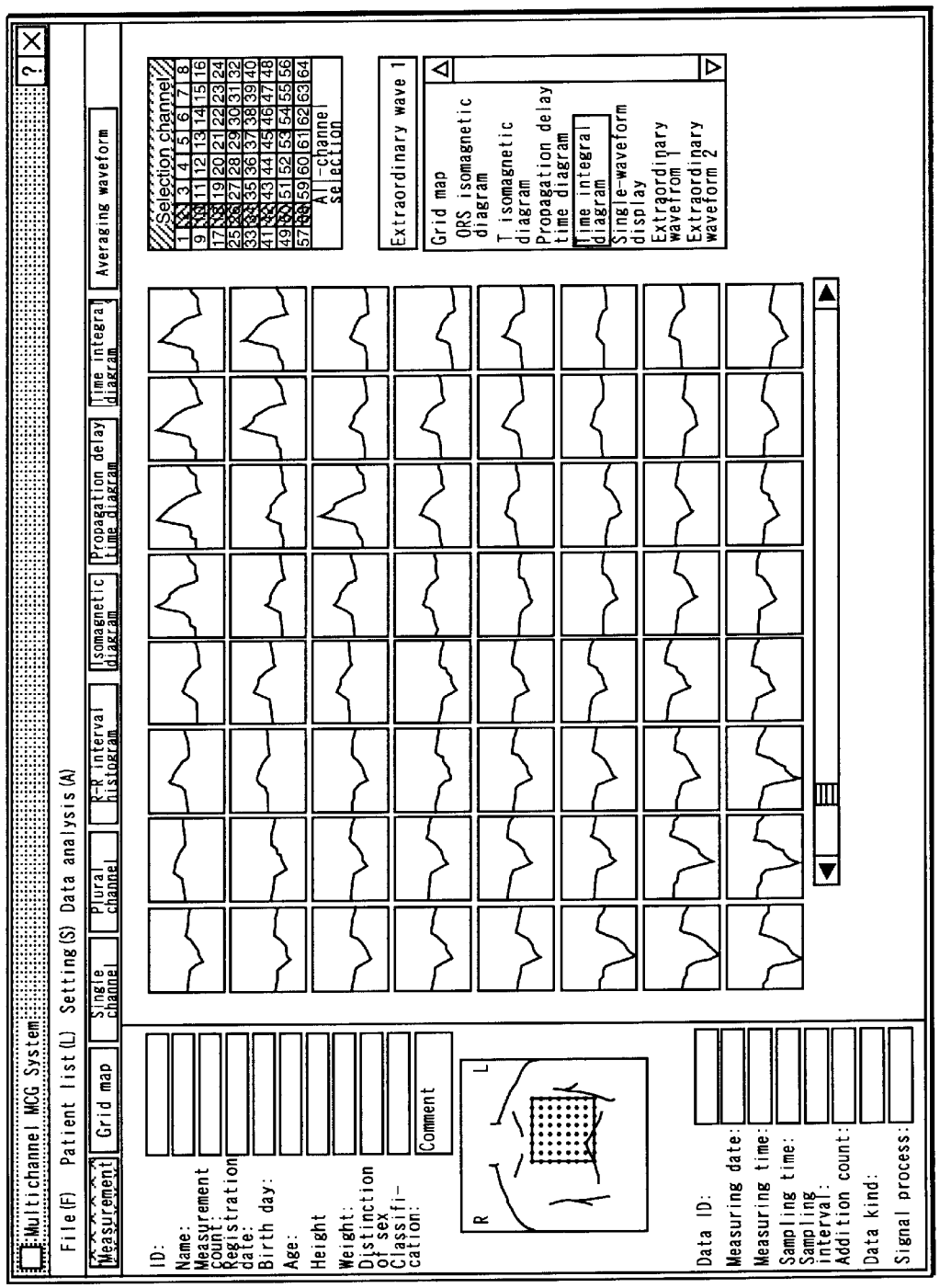
FIG. 23 shows a grid map display example of abnormal waveforms.

FIG. 23 shows an example that since the difference degree Δ from the waveform Y registered as a reference waveform is large, the signal data registered in the extraordinary wave buffer is displayed in a grid map. When regular heartbeat data is registered as a reference waveform as shown in FIG. 3, an irregular signal such as an irregular pulse or external magnetic field noise is registered in the data analysis menu in the name of "abnormal waveform" via evaluation of the difference degree from the reference waveform and furthermore, when there are a plurality of abnormal waveforms, a discrimination number is automatically added behind "abnormal waveform" such as "abnormal waveform 1", "abnormal waveform 2", - - - . When these items are designated from the data analysis menu, the waveform is displayed in a grid map.

When the averaging process is not normally performed for signal data and "QRS isomagnetic diagram" is selected, it cannot be reconfigured and an error dialog is displayed. When the OK button is pressed in this case, the screen is moved to the screen shown in FIG. 13 but no isomagnetic diagram is displayed, and line cursors of the designated number are displayed in the time waveform area of the reference channel. When the line cursors are moved by the mouse and the position is ascertained by the Enter key, a "QRS isomagnetic diagram" of the abnormal waveform is reconfigured.

Figure 24:
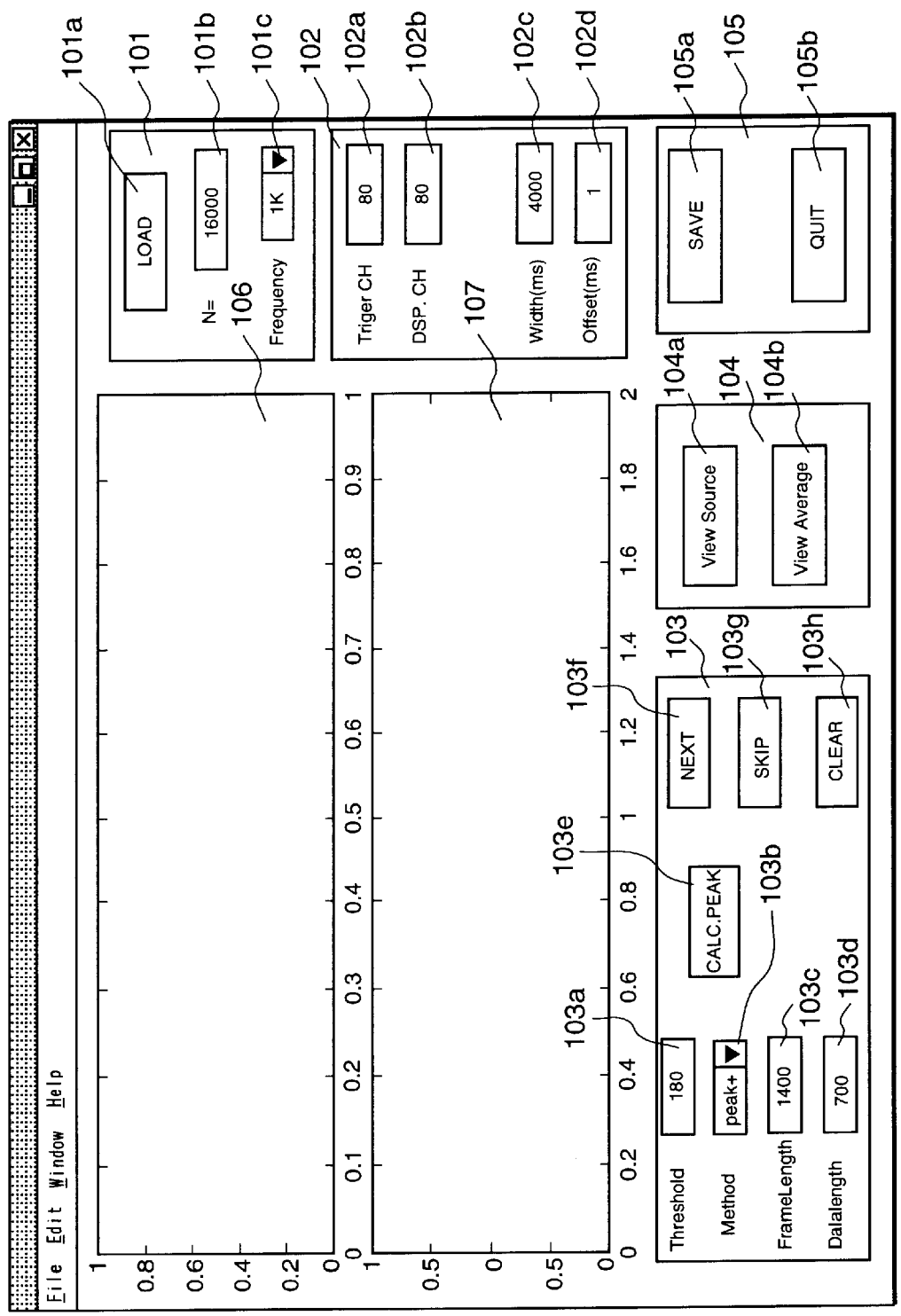
FIG. 24 shows a display example of the initial screen of the average screen.

Another embodiment of the averaging process will be explained in detail hereunder by referring to FIGS. 24 to 31. FIG. 24 shows a display screen of the averaging process program. The display screens shown in FIGS. 24 to 31 show the analysis data unit 805 and the operation area unit 806 shown in FIG. 5 in detail. Each screen is mainly divided into five object groups. When each object group is indicated according to the procedure of the analysis process, in the operation area unit, a data read object 101, a graph display control object 102, an averaging object 103, an all-channel outline display object 104, and a file storage and termination object 105 are arranged. On the upper part of the display screen, an original waveform (the measured magnetic field waveform is referred to as an original waveform) display area 106 is arranged and on the lower part of the display screen, an averaging display area 107 is arranged. An embodiment of the operation method will be explained hereunder according to the operation procedure.

Figure 25:
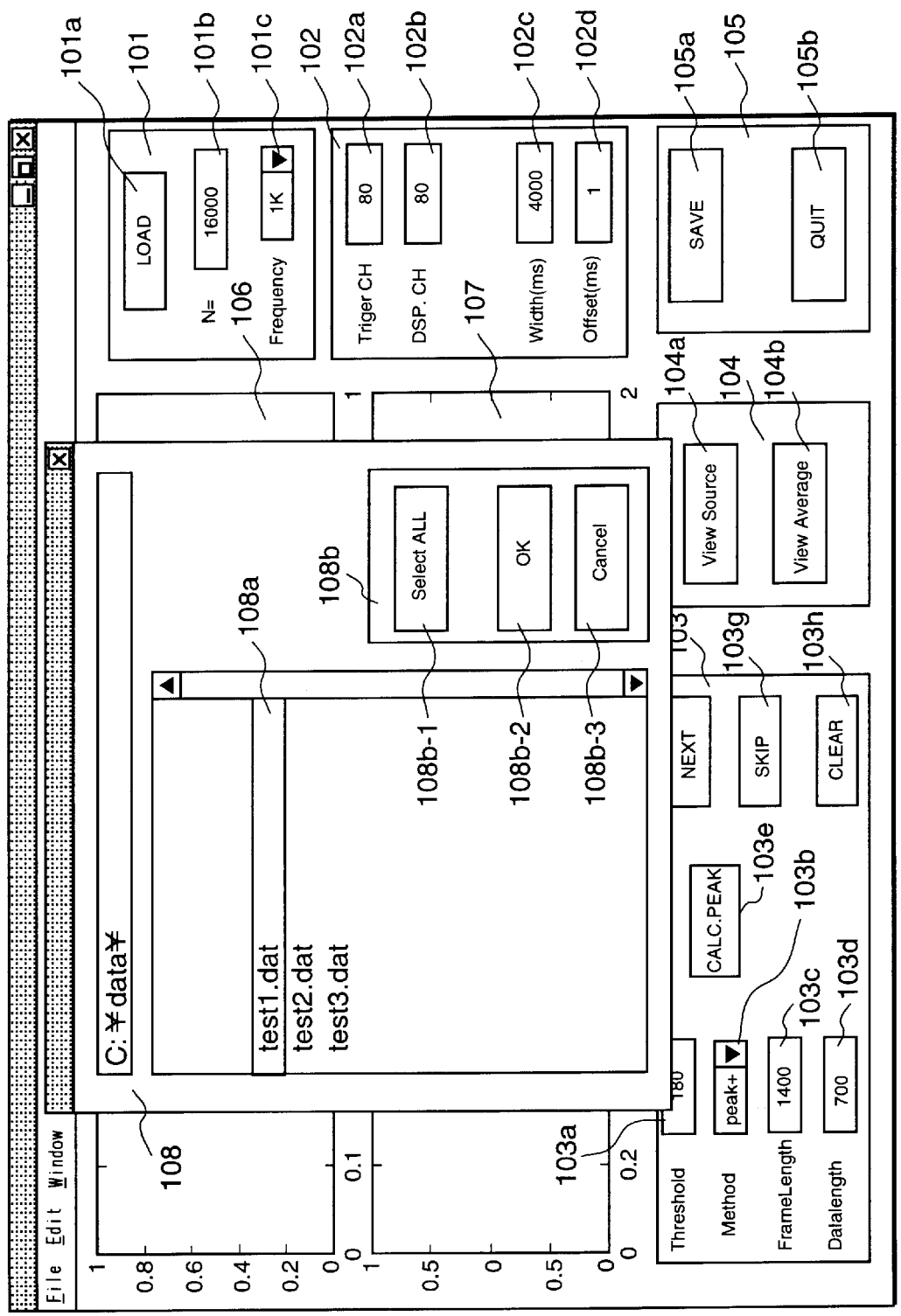
FIG. 25 shows a display example of the file selection screen of the average screen.

An embodiment of file reading will be explained by referring to FIG. 25. With respect to file reading, when the button LOAD 101a is pressed, the file selection dialog 108 is displayed, and the icon is moved to the position of the selected file name to select the file name, and file selection is set. According to this embodiment, the file named with test1.dat is selected and it is legibly displayed by the highlight 108a. When all the files are to be selected, by selecting the Select All button 108b-1 among the selection buttons 108b, all the files are highlighted and all the files can be selected. When a plurality of files are selected, a plurality of windows shown in FIG. 1 are displayed. After one or more files are selected as mentioned above, the OK button 108b-2 is pressed and the program is moved to the next mode. When the file selection dialog 108 is opened by mistake, the Cancel button 108b-3 is selected and the screen can be returned to the display screen shown in FIG. 24. The number of data to be read from the selected file can be set by inputting the numerical value to the data points input window 101b. The data sampling frequency of the selected file is selected by the Frequency toggle 101c. According to this embodiment, a sampling frequency of 1 kHz is selected. When a manual selection method like the Frequency toggle 101c is troublesome, for example, the information of the sampling frequency at the time of measurement may be recorded in the selected file together with the measured data and the sampling frequency automatically decided.

Figure 26:
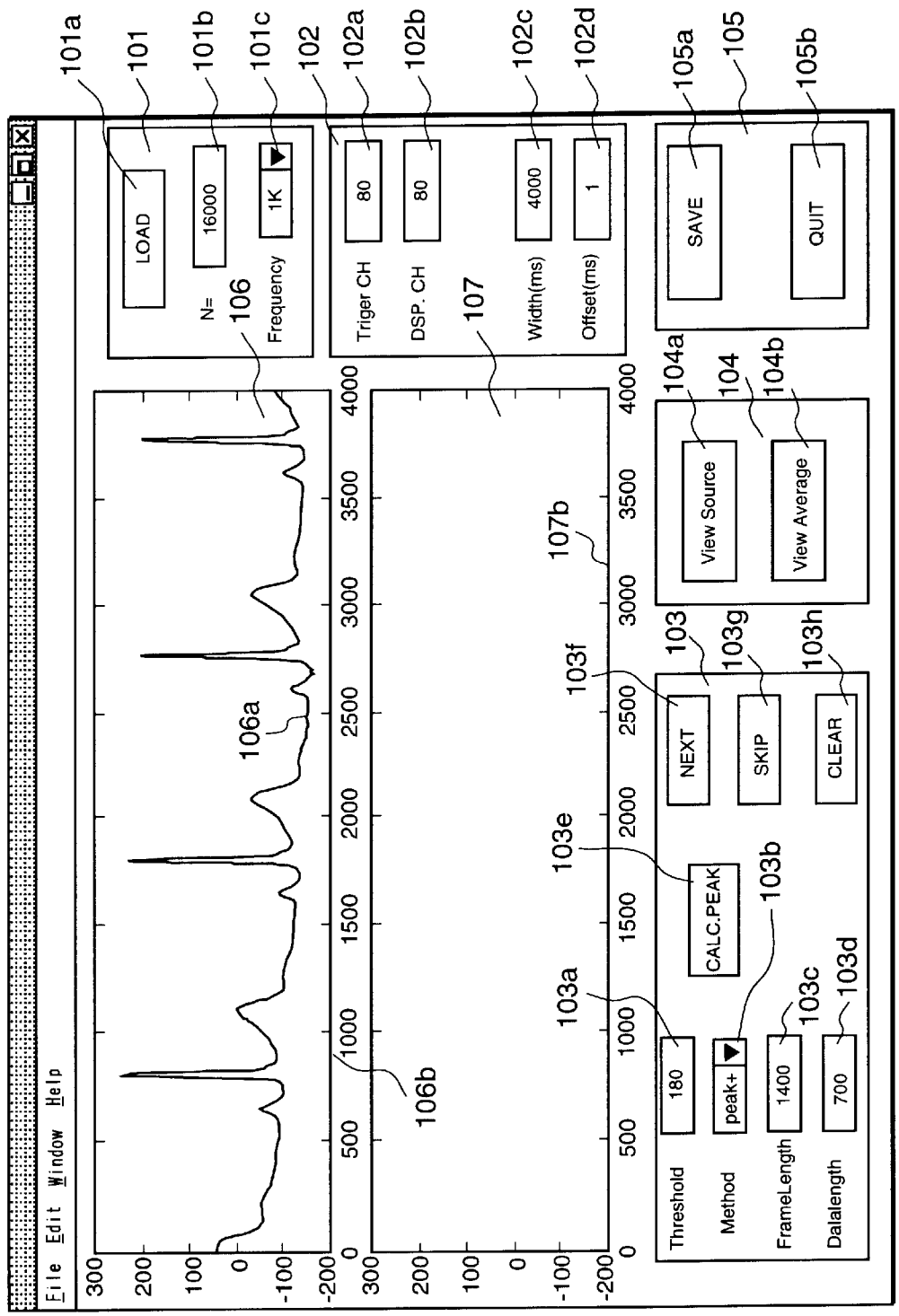
FIG. 26 shows a raw waveform display screen of the average screen.

Graph display control will be explained by referring to FIG. 26. The waveform 106a displayed in the original waveform display area 106 shown in FIG. 26 is the waveform of the channel (channel 80 in this embodiment) selected by the Trig.ch button 102a in the file test1.dat selected by the highlight 108a in FIG. 25. In this embodiment, in addition to the 64 magnetic sensors shown in FIG. 2, external inputs of 16 channels are provided, and in the 80th channel, the waveform (described later in FIG. 32) of the second inductive electrocardiogram measured at the same time with the magnetrocardiograph waveform is fetched, and the display screen that the averaging process is performed using the waveform of the electrocardiogram is displayed. Needless to say, the channels selected by the Trig.ch button 102a are not limited to the electrocardiogram waveforms of the 80 channels, but an optional channel of the magnetrocardiograph waveforms shown in FIG. 6 can be selected. The Dsp.ch button 102b can select the channel (channel 80 in this embodiment) displayed in the averaging display area 107. According to this embodiment, the channels selected in the original waveform display area 106 and the averaging display area 107 are the same. However, they may not be the same always. The graph display areas (time area width) of the original waveform display area 106 and the averaging display area 107 can be changed by inputting numerical values to the text box width 102c and the text box offset 102d.

The text box width 102c sets the time widths (in units of ms) displayed in the horizontal axes 106b and 107b of the original waveform display area 106 and the averaging display area 107 and the text box offset 102d can set the time to be skipped (in units of ms). For example, when skipping the data width 1000 ms from the data point of time 0 and reading the data width 4000 ms, a numerical value of 1000 ms is input to the text box offset 102d and a numerical value of 4000 ms is input to the text box width 102c. In this embodiment, an example that a numerical value of 1 ms is input to the text box offset 102d and a numerical value of 4000 ms is input to the text box width 102c is shown. The vertical axes of the original waveform display area 106 and the averaging display area 107 in this embodiment are indicated by data values which are converted to digital data by the A-D converter. However, they may be indicated by the value of strength of the magnetic field or potential. Furthermore, according to this embodiment, the display width of the vertical axis is structured so as to be automatically scaled within the range that the maximum value and minimum value of the data in the time width which is selected in the display section can be displayed.

The peak detection setting method will be explained hereunder by referring to FIG. 27. Peak detection is executed by the averaging object 103. A numeral is input into the text box Threshold 103a first and the peak detection threshold (180 in this embodiment) is set. Next, the detection method is set by the toggle button Method 103b. There are four kinds of methods available, such as a method (peak+, described in FIG. 27) for detecting the maximum peak having a value larger than the threshold, a method (peak−) for detecting the minimum peak having a value smaller than the threshold, a method (cross+) for detecting the cross point with the threshold when the peak value changes from a value smaller than the threshold to a value larger than the threshold, and a method (cross−) for detecting the cross point with the threshold when the peak value changes from a value larger than the threshold to a value smaller than the threshold, In this embodiment, the method (peak+) for detecting the maximum peak is selected. Furthermore, the time width to be averaged can be selected by entering a numeral in the text box FrameLength 103c. By inputting a numeral to the text box DataLength 103d, the time width before peak detection can be set. When the peak is to be detected by the set content (103a, 103b, 103c, 103d), the button CALC.PEAK 103a is pressed to perform calculation. Immediately after termination of the peak detection, the set values of the FrameLength 103c and the DataLength 103d are displayed in the original waveform display area 106 and the setting range is displayed on the original waveform 106a by the averaging display range display unit B1, the averaging display range maximum time B2, and the averaging display range minimum time B3.

For all the peak points extracted in the waveforms on the display screen, white defect circle marks C1, C2, C3, and C4 are displayed. Above the circle mark C1, number 1 is displayed so as to find what peak is detected. According to this embodiment, the value of the FrameLength 103c is set at 1400 and the value of the DataLength 103d is set at 700. When the averaging process is to be performed by ascertaining the original waveform 106a displayed in the original waveform display area 106 and the averaging display range display unit B1, the averaging display range maximum time B2, and the averaging display range minimum time B3, the button NEXT 103f is pressed. The averaging process is performed and the averaging result is displayed in the averaging display area 107 as an averaging waveform 107a. FIG. 27 shows an example that the waveform of the circle mark C1 is observed, and then the button NEXT 103f is pressed and the averaging process is performed. The averaging waveform 107a displayed is the same as the waveform at the center of the circle mark C1 because the averaging count is one. The averaging process is also performed for all the waveforms of the channels which are not displayed in the displayed original waveform display area 106 or the averaging display area 107 at the same time. In FIG. 27, only one waveform is displayed in the original waveform display area 106 and in the averaging display area 107 respectively, though a plurality of waveforms may be displayed in the original waveform display area 106 and in the averaging display area 107 respectively.

Figure 27:
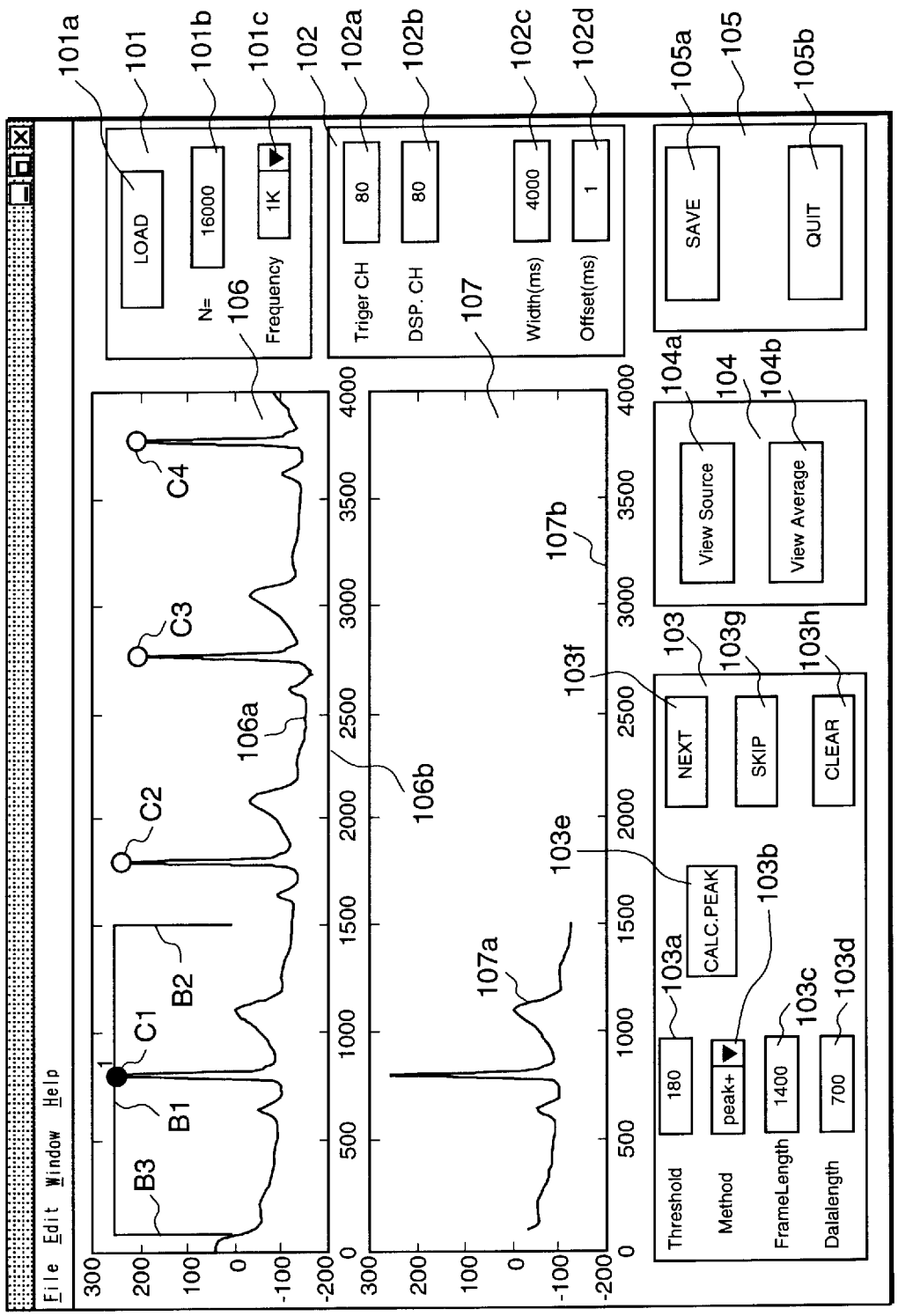
FIG. 27 shows an averaging process setting screen of the average screen.
Figure 28:
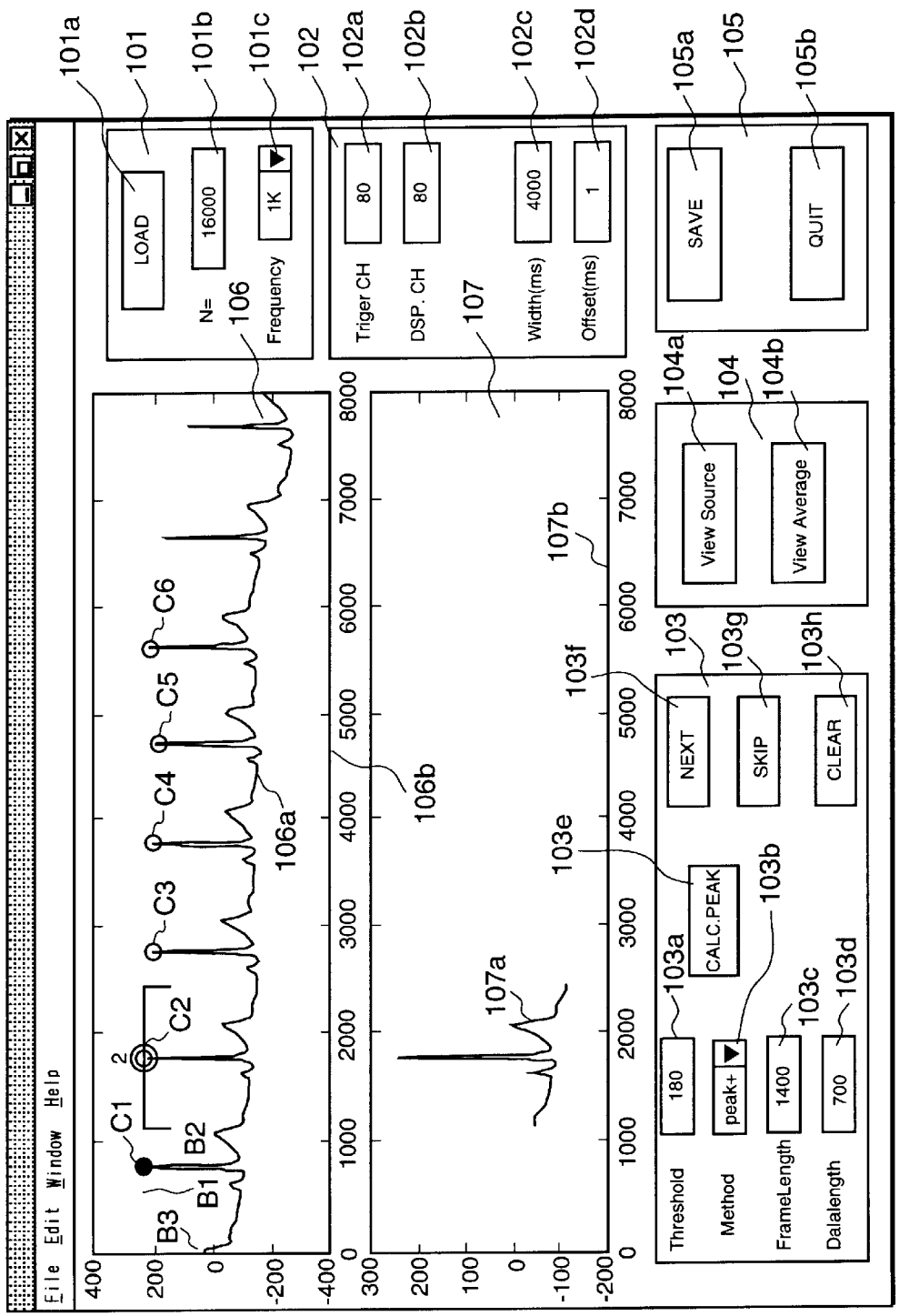
FIG. 28 shows an average processing screen of the average screen.

FIG. 28 shows a case that the second peak is not selected as averaging data by pressing the button SKIP 103g. Furthermore, FIG. 28 shows a case that after the button SKIP 103g is pressed, the numeral 4000 of the text box width 102c for setting the waveform display time width is changed to 8000. Therefore, the averaging waveform 107a displayed in the averaging display area 107 is the first waveform itself selected in FIG. 27. When the peak selection process is to be interrupted, by pressing the button CLEAR 103h, the averaging waveform 107a displayed in the averaging display area 107 is erased and nothing is displayed in the averaging display area 107. For the peak selected for the averaging process, the circle mark C1 is changed from white defect to black circle and for the peaks not selected for the averaging process, the mark is changed to a double circle mark. Needless to say, the shape and color of circle marks are not limited to white or black and circle. As mentioned above, when the averaging selection state of each peak point is left as a history, it can be checked again after termination of the averaging process and furthermore, although not clearly stated in this embodiment, after termination of all the processes, averaging waveforms of unnecessary peaks can be selected and removed.

Figure 29:
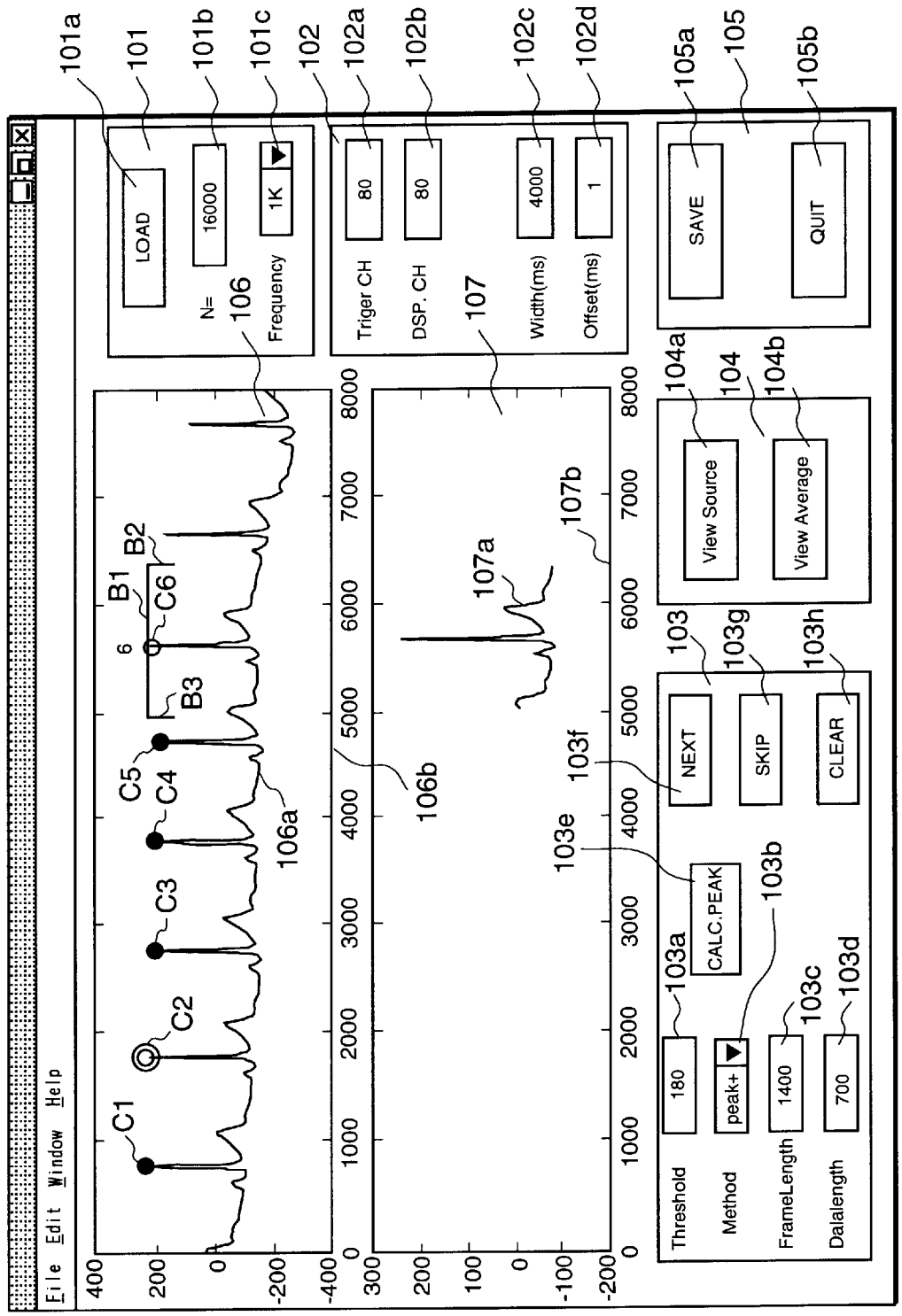
FIG. 29 shows an average processing screen of the average screen.

An embodiment when the averaging process shown in FIG. 27 or 28 is continued and the same process is performed for the sixth detected peak is shown in FIG. 29. Since the text button Threshold 103a is set at 180 and the torque button Method 103b is set at the method (peak+) for detecting the maximum peak, the peaks before the sixth peak are not detected because the peak value is less than 180. Furthermore, when peaks are to be detected at the next time width, if the value of the text box offset 102d, for example, 8000 is input, the waveform from 8000 ms to 16000 ms is displayed and the same averaging process can be performed. As mentioned above, C1, C3, C4, C5, and C6 of black circles among the circle marks C1 to C6 indicate peaks selected for the averaging process and the white defect double circle mark C2 indicates a peak not selected for the averaging process.

Figure 30:
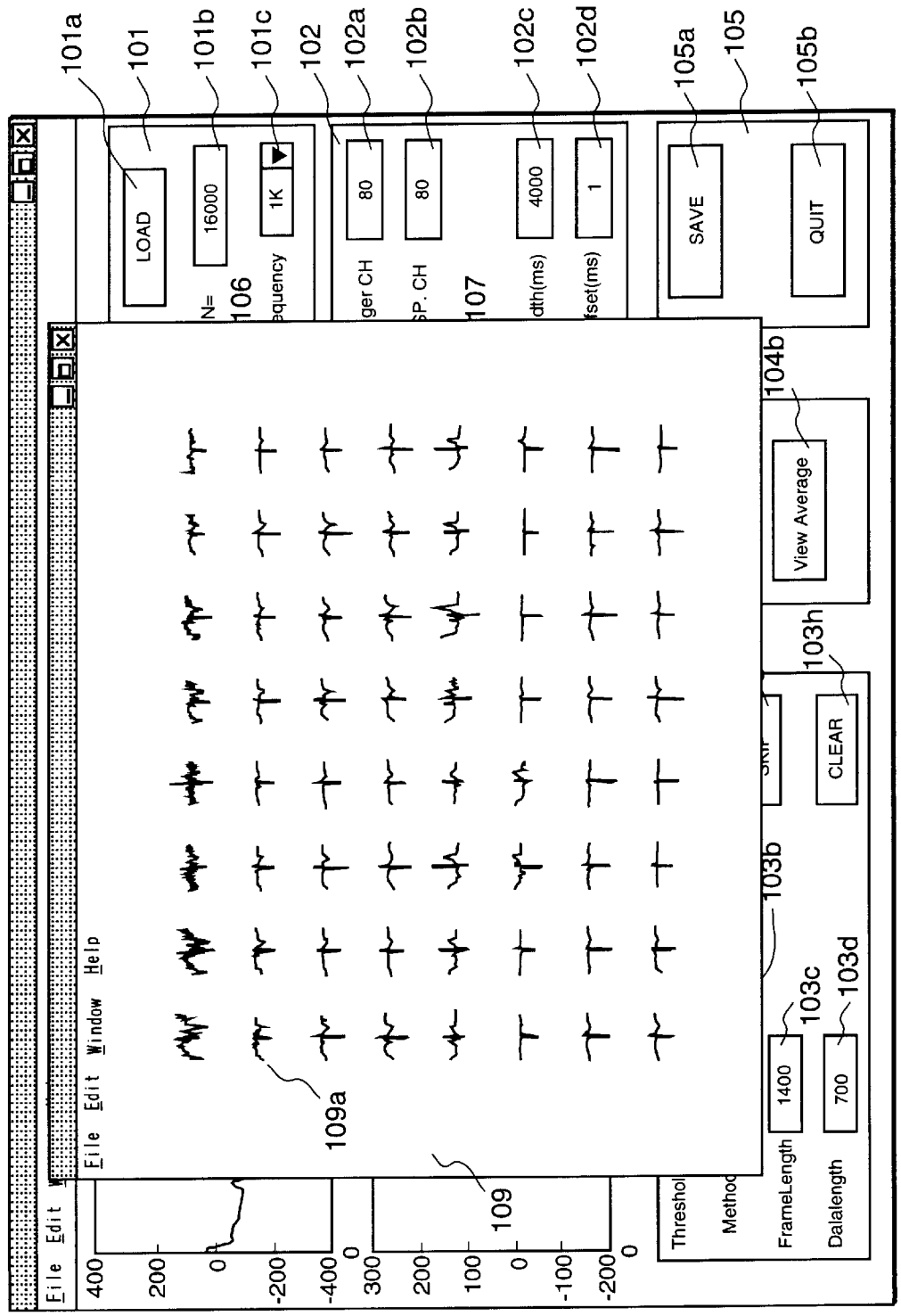
FIG. 30 shows an overall waveform display screen of the average screen.

FIG. 30 shows a waveform display 109 of averaging process results of all the channels when the button View Average 104b of the all-channel outline display object 104 is pressed. By this operation, the waveform 109a for which the all-channel averaging process is performed can be displayed in correspondence with the sensor position. In the same way, by pressing the button View Source 104a, the waveforms of all the channels before processing can be displayed.

Figure 31:
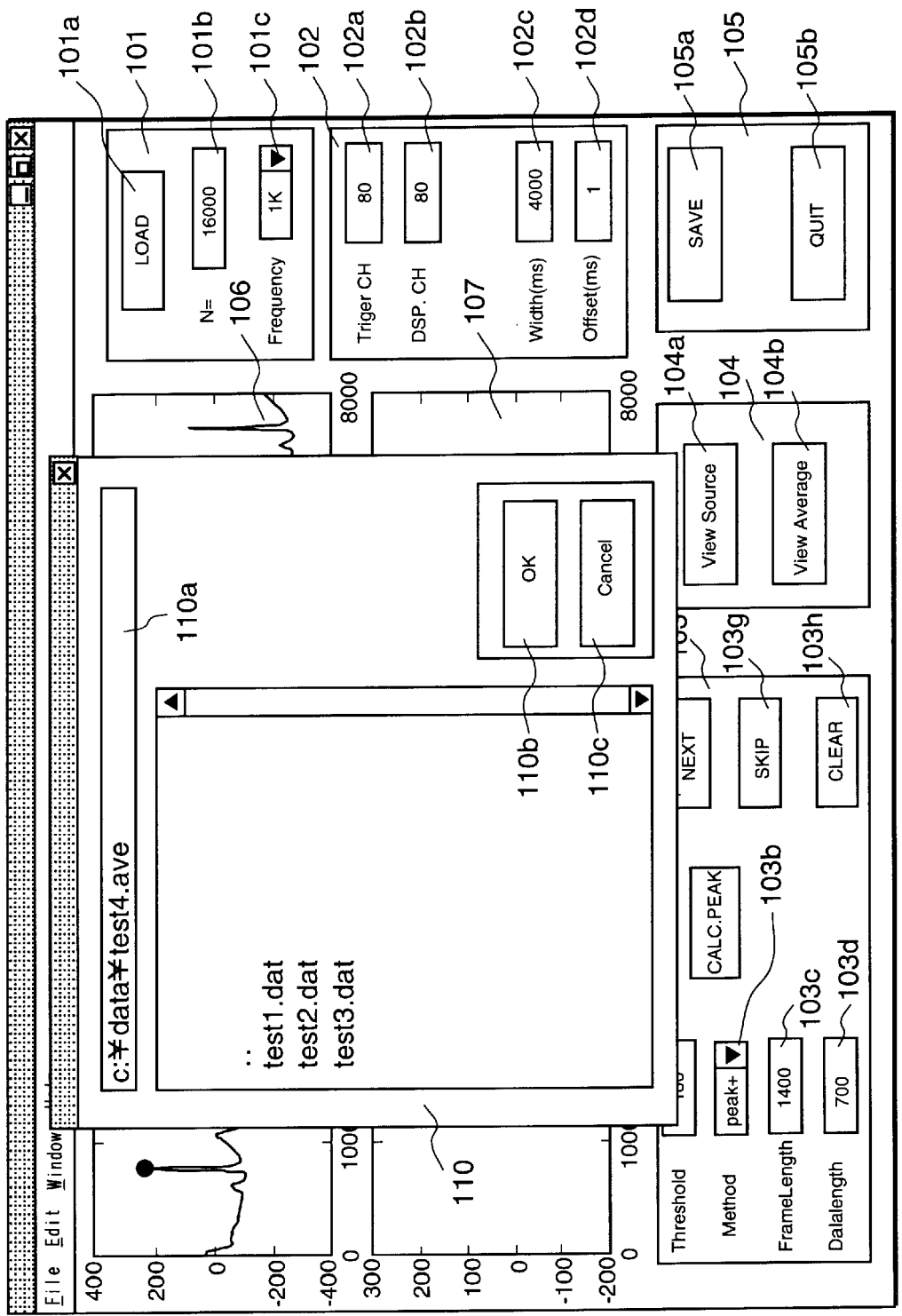
FIG. 31 shows a file retention process screen of the average screen.

FIG. 31 shows a drawing for explaining the waveform file saving process after the averaging process. When saving the file after the averaging process, the button SAVE 105a is pressed and the saving dialog 110 is displayed. When a file name is to be newly prepared after display, by inputting the file name to the text box 110a and pressing the button OK 110b, the file can be saved in an optional file name. When a file is to be overwritten and saved in an existing file, the file name to be used is highlighted, the button OK 110b is pressed, and the averaging result can be saved as the same file. When the saving dialog 110 is displayed by mistake or no data is to be saved in the file, by pressing the button Cancel 110c, no data is saved in the file and the screen can be returned to the display screen shown in FIG. 31. When all the processes are finished, by pressing the button QUIT 105b, the application of the averaging process can be finished.

The aforementioned are the procedure for performing the averaging process and the screen display method. When performing the averaging process, if the pre-process is performed as specified below, an appropriate averaging process can be performed. When the base line of the waveform sways due to magnetic field noise of low frequency component such as breathing noise, it is desirable to pass a signal of one channel or signals of all channels through the high-pass filter as a pre-process of the averaging process. When a signal of only one channel passes through the high-pass filter, peak detection is executed for the signal passing through the high-pass filter, and from the peak detection result, the averaging process can be performed for the signals of all the channels. As a filter kind used for the high-pass filter, for example, a high-pass filter having a cut-off frequency within the range from 0.1 to 3 Hz, or a digital filter such as an IIR (infinite impulse response) filter or an FIR (finite impulse response) filter, may be used. When as other noises, commercial power noise (for example, 50 Hz, 60 Hz) and low frequency breathing noise become problems, a comb line notch filter (a filter for removing a frequency integer times of 50 Hz or 60 Hz) can be used. A comb line notch filter is a notch filter having a band width of about 1 Hz centering on the frequency of 0 Hz, 50 Hz, 100 Hz, 150 Hz, - - - . When the aforementioned filtering process is used as a pre-process of the averaging process, the averaging process having less noise may be available.

Figure 32:
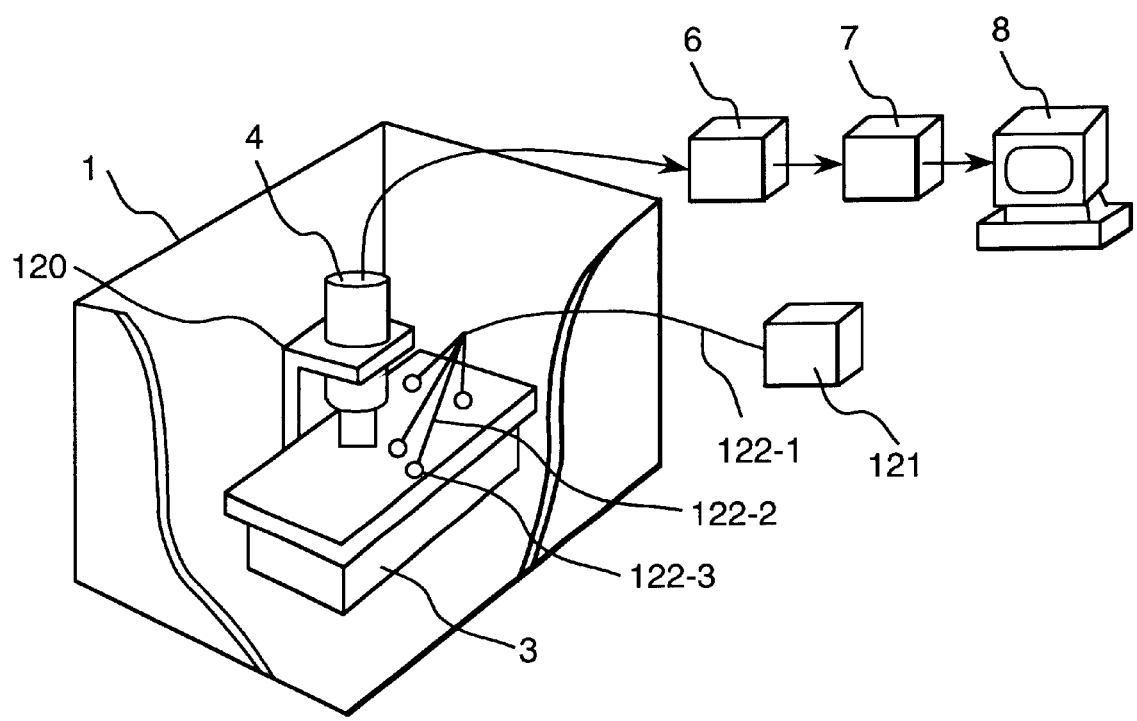
FIG. 32 is a drawing showing arrangement and connection of an electrocardiograph of a physiological magnetic field measuring instrument.

Next, when the averaging process is to be performed by an electrocardiogram, a constitution that a magnetocardiogram and an electrocardiogram are measured at the same time will be explained by referring to FIG. 32. An electrocardiograph body 121 is arranged outside the shield room so as to avoid magnetic noise. A cable 122-1 of the electrocardiograph connected to the electrocardiograph body 121 is inserted into the shield room and to the end of the cable 122-1 of the electrocardiograph, a four-leg inductive cable 122-2 is connected. At the end of the four-leg inductive cable 122-2, a carbon electrode 122-3 hardly generating magnetic noise is arranged. In this embodiment, the four-leg inductive cable 122-2 and the carbon electrode 122-3 are used for explanation. However, the embodiment is not limited to them and for example, a carbon electrode may be used for the 12-lead ECG wire and the electrode unit may be composed of a nonmagnetic material. Furthermore, the 12-lead ECG wire and the electrocardiograph body 121 may be arranged in the rack where the FLL circuit 6 and the amplifier, filter, and amplifier 7 are housed. The waveform of the electrocardiograph is stored on the calculator 9 as digital data at the same time with the waveform of magnetocardiograph and waveforms of optional number of magnetrocardiograph or electrocardiograph can be displayed in real time at the same time with reading of data of the magnetocardiograph or electrocardiograph. The display unit of real-time waveforms is not limited to one screen of the calculator 8 and real-time waveforms can be displayed on a plurality of screens (computer display, television monitor, etc.) selectively and simultaneously inside or outside the shield room.

Figure 33A:
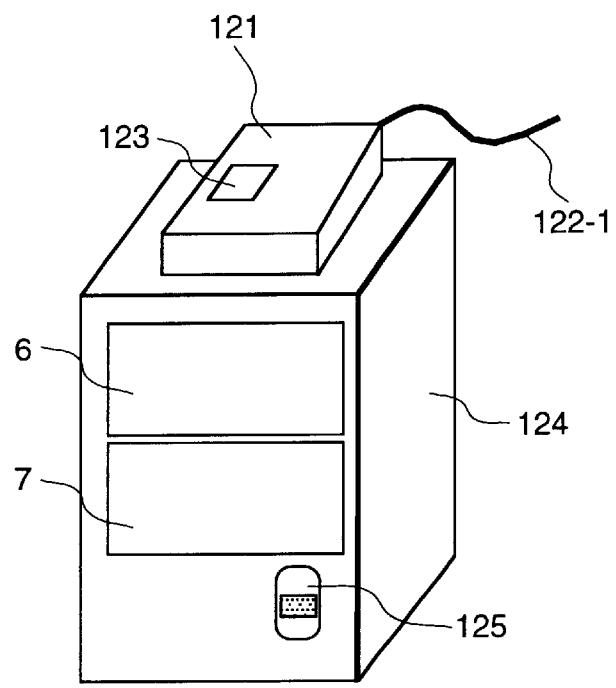
FIGS. 33A and 33B are drawings showing arrangement of an electrocardiograph of a physiological magnetic field measuring instrument.
Figure 33B:
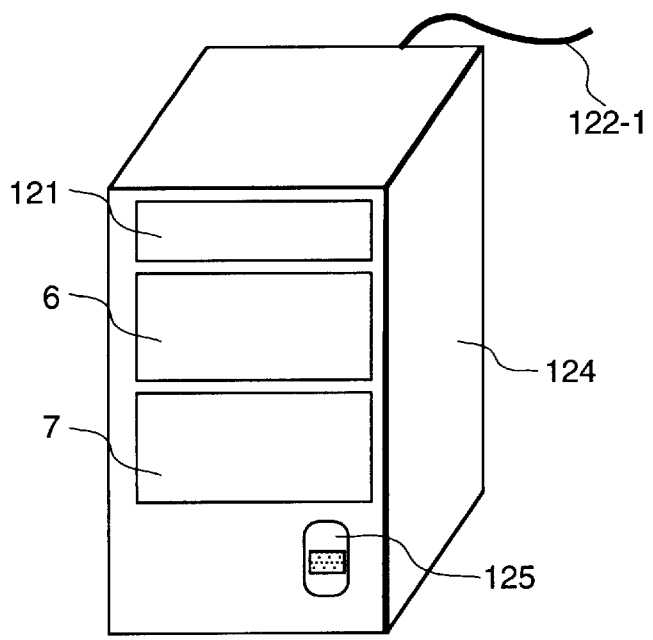

FIGS. 33A and 33B show two embodiments of the arrangement relationship between the electrocardiograph body 121 and the physiological magnetic field measuring instrument. FIGS. 33A and 33B show the location relationship between the FLL circuit 6 and the amplifier, filter, and amplifier 7 which are arranged outside the shield room 1 indicated in the embodiment of the physiological magnetic field measuring instrument shown in FIG. 1 and the electrocardiograph body 121. In the embodiment shown in FIG. 33A, the FLL circuit 6 and the amplifier, filter, and amplifier 7 are built in the box 124 as one unit and when the power switch 125 is turned ON, the powers of the FLL circuit 6 and the amplifier, filter, and amplifier 7 are turned ON in a batch. On the upper part of the box 124, the electrocardiograph body 121 is installed, connected to the cable 122-1, and introduced into the shield room. The cable 122-1 and the cable connected between the FLL circuit 6 and the cryostat 4 may be laid in the shield room via the same hole bored in the shield room wall. When the magnetic noise due to the electromagnetic wave induced by the cable of the electrocardiograph becomes a problem, the cable 122-1 and the cable connected between the FLL circuit 6 and the cryostat 4 may be separately laid in the shield room via different holes bored in the shield room wall. A roll paper 123 for printing the waveform of an electrocardiogram is prepared in the electrocardiograph body 121. The waveform printed on the roll paper 123 is not limited to the waveform of an electrocardiogram, but the waveform of magnetocardiograph may be printed, and a roll paper unit only for printing the waveform of the magnetocardiograph may be installed in the box 124. In the embodiment shown in FIG. 33B, the FLL circuit 6, the amplifier, filter, and amplifier 7, and the electrocardiograph body 121 are built in the box 124 as one unit.

What is claimed is:

1. A physiological magnetic field measuring instrument for measuring a magnetic field at plural positions of a living body of a patient generated from the inside of said living body, comprising:

means for assigning discrimination information to measuring conditions necessary for measuring a physiological magnetic field; and means, when measuring said physiological magnetic field, for setting measuring conditions corresponding to said discrimination information so as to be read by designating said discrimination information as an input to said physiological magnetic field measuring instrument.

2. A physiological magnetic field measuring instrument according to claim 1, further comprising a selection display unit for displaying for designation said discrimination information via a display screen displaying measured data of said physiological magnetic field.

3. A physiological magnetic field measuring instrument for measuring a magnetic field at plural positions of a living body of a patient generated from the inside of said living body, comprising:

means for assigning discrimination information to a data analysis method to be executed with respect to measured data relating to a physiological magnetic field and to corresponding data analysis parameters required to execute the data analysis method; and means for setting a data analysis by said data analysis parameters and said data analysis method corresponding thereto so as to be executed by designating said discrimination information as an input to said physiological magnetic field measuring instrument.

4. A physiological magnetic field measuring instrument for measuring magnetic fields at a plurality of positions generated from the inside of a living body of a patient using a plurality of magnetic sensors comprising:

channel display means for displaying channels corresponding to said plurality of magnetic sensors on a display screen, channel designation means for designating a channel from said channel display means, time waveform display means for displaying measurement signals of said designated channel as time waveforms on one screen across a plurality of lines of time axes; and bar graph display means for displaying a time interval between a peak and a peak of a characteristic time waveform repeatedly appearing on said time axis by a bar graph on said time waveform display screen;

further comprising:

discrimination display means for displaying so as to discriminate, when a bar graph is designated from a display area of said bar graph, said designated bar graph and a part of a peak interval of a time waveform corresponding to said designated bar graph.

* * * * *